US006838592B1

(12) United States Patent
Nixon et al.

(10) Patent No.: US 6,838,592 B1
(45) Date of Patent: Jan. 4, 2005

(54) METHODS FOR THE IDENTIFICATION OF COMPOUNDS FOR THE TREATMENT OF ALZHEIMER'S DISEASE

(75) Inventors: Ralph A. Nixon, Tarrytown, NY (US); Anne M. Cataldo, Nanuet, NY (US); Paul M. Mathews, Irvington, NY (US)

(73) Assignee: Nathan S. Kline Institute for Psychiatric Research, Orangeburg, NY (US)

( * ) Notice: Subject to any disclaimer, the term of this patent is extended or adjusted under 35 U.S.C. 154(b) by 0 days.

(21) Appl. No.: 09/560,124

(22) Filed: Apr. 28, 2000

Related U.S. Application Data

(60) Provisional application No. 60/140,643, filed on Jun. 23, 1999, provisional application No. 60/140,644, filed on Jun. 23, 1999, provisional application No. 60/131,890, filed on Apr. 30, 1999, and provisional application No. 60/131,991, filed on Apr. 30, 1999.

(51) Int. Cl.[7] .......................... G01N 33/00; A01K 67/00; A01K 67/033; C12N 5/00; C12N 15/63
(52) U.S. Cl. ...................... 800/3; 800/8; 800/9; 800/12; 800/18; 435/325; 435/455
(58) Field of Search .............................. 800/3, 8, 9, 12, 800/18; 435/325, 455, 4, 366, 368; 424/9.1

(56) References Cited

PUBLICATIONS

Mullins et al. Fulminant hypertension in transgenic rats harbouring the mouse Ren–2 gene pp. 541–544 vol. 344 1990.*
Mullins et al. Expression of the DBA/2J ren gene in the adrenal gland of transgenic mice pp. 4065–4072 1989.*
Sigmund Viewpoint: are studies in genetically altered mice out of control pp. 1425–1429 2000.*
Wall Transgenic livestock: progress and prospects for the future pp. 57–68 1996.*
Hammer et al. Spontaneous inflammatory disease in transgenic rats expressing HLA–B27 and human B2m: an animal model of HLA_B27–associated human disorders pp. 1099–1112 1990.*
Taurog et al. HLA–B27 in inbred and non–inbred transgenic mice pp. 4020–4023 No. 11. 1988.*
Bucci et al., The Small GTPase rab5 Functions as a Regulatory Factor in the Early Endocytic Pathway, Cell 70:715–28, 1992.
Stenmark et al. Inhibition of rab5 GTPase Activity Stimulates Membrane Fusion in Endocytosis EMBO Journal 13:1287–1296, 1994.
Stenmark et al Rabaptin–5 is a Direct Effector of the Small GTPase Rab5 in Endocytic Membrane fusion, Cell 83:423–32, 1995.
Bjarnadottir et al., "Intracellular Accumulation of the Amyloidogenic L68Q Variant of Human Cystatin C in NIH/3T3 Cells," Journal of Clinical Pathology: Molecular Pathology 51:317–326 (1998).
Busca et al., "The Carboxy–Terminal Region of Human Lipoprotein Lipase is Necessary for its Exit From the Endoplasmic Reticulum," Journal of Lipid Research 39:821–833 (1998).

Cataldo et al., "Increased Neuronal Endocytosis and Protease Delivery to Early Endosomes in Sporadic Alzheimer's Disease: Neuropathologic Evidence for a Mechanism of Increased β–Amyloidogenesis," Journal of Neuroscience 17:6142–6151 (1997).
Cataldo et al., "Lysosomal Hydrolases of Different Classes are Abnormally Distributed in Brains of Patients with Alzehimer Disease," Proceedings of the National Academy of Sciences (USA) 88:10998–11002 (1991).
Cataldo et al., "Lysosomal Abnormalities in Degenerating Nuerons Link Neuronal Compromise to Senile Plaque Development in Alzheimer Disease," Brain Research 640: 68–80 (1994).
Cataldo et al., "Properties of the Endosomal–Lysosomal System in the Human Central Nervous System: Disturbances Mark Most Neurons in Populations at Risk to Degenerate in Alzehimer's Disases," Journal of Neuroscience 16:186–199 (1996).
Dash et al., "Inhibitors of Endocytosis, Endosome Fusion, and Lysosomal Processing Inhibit the Intracellular Proteolysis of the Amyloid Precursor Protein," Neuroscience Letters 164:183–186 (1993).
Granholm et al., "Segmental Trisomy Ts65Dn Mice Have a Decrease in Nerve Growth Factor Receptors in Septal Forebrain Neurons," Abstracts, Society for Neuroscience 24:2008, Abstract 803.4 (1998).
Haas et al., "Targeting of Cell–Surface β–Amyloid Precursor Protein to Lysosomes: Alternative Processing into Amyloid–Bearing Fragments," Nature 357:500–503 (1992).
Holtzman et al., "Development91 Abnormalities and Age–Related Neurodegeneration in a Mouse Model of Down Syndrome," Proceedings of the National Academy of Sciences (USA) 93:13333–13338 (1996).
Ikegami et al., "Immunohistochemical Examination of Phosphorylated Tau in Granulovacuolar Degeneration Granules," Psychiatry and Clinical Neurosciences 50: 137–140 (1996).
Korenberg, "Mental Modelling," Nature Genetics 11:109–111 (1995).
Punnonen et al., "Effects of Vinblastine, Leucine, and Histide, and 3–Methyladenine on Autophagy in Ehrlich Ascites Cells," Experimental & Molecular Pathology 52:87–97 (1990).
Reeves et al., "A Mouse Model for Down Syndrome Exhibits Learning and Behaviour Deficits," Nature Genetics 11:177–183 (1995).
Watari et al., "Niemann–Pick C1 Protein: Obligatory Roles for N–Terminal Domains and Lysosomal Targeting in Cholesterol Mobilization," Proceedings National Academy Sciences 96:805–810 (1999).
Yan Zhou et al., "A Mutation in a Mild Form of Galactosialidosis Imparis Dimerization of the Protective Protein and Renders it Unstable," EMBO Journal 10:4041–4048 (1991).

* cited by examiner

*Primary Examiner*—Anne-Marie Falk
(74) *Attorney, Agent, or Firm*—Kristina Bieker-Brady; Clark Elbing LLP

(57) ABSTRACT

The invention features methods for identifying compounds useful for the treatment of Alzheimer's disease.

7 Claims, 18 Drawing Sheets lipofuscin autofluorescence

Cathepsin D Immunohistochemistry

Cat D Western blot analysis

Cat D activity

METHODS FOR THE IDENTIFICATION OF COMPOUNDS FOR THE TREATMENT OF ALZHEIMER'S DISEASE

CROSS-REFERENCE TO RELATED APPLICATIONS

This application claims benefit to U.S. Provisional Application Nos. 60/131,890 (filed Apr. 30, 1999), 60/131,991 (filed Apr. 30, 1999), 60/140,643 (filed Jun. 23, 1999), and 60/140,644 (filed Jun. 23, 1999), each hereby incorporated by reference.

STATEMENT AS TO FEDERALLY SPONSORED RESEARCH

The invention was supported in part by National Institutes of Health grant AG 10916. The government has certain rights to the invention.

BACKGROUND OF THE INVENTION

The invention relates to methods for identifying compounds useful in the treatment of Alzheimer's disease (AD).

Abnormalities of the neuronal endocytic pathway (EP) are the earliest cellular manifestation of sporadic AD (SAD) yet demonstrated. Importantly, EP abnormalities distinguish SAD from certain other subtypes of AD caused by presenilin mutations.

Early endosomes are the site of internalization and initial processing of amyloid precursor protein (APP) and apolipoprotein E (ApoE). They are also a major site of both amyloid β peptide (Aβ) formation and mediate the cellular uptake of Aβ and soluble APP. Individual neuronal endosomes can be as much as 32-fold larger in volume than the normal average and the total endosome volume can be 3-fold higher in SAD brain. Because of a concurrent activation of the lysosomal system (LS), lysosomal acid hydrolases (including proteases) are targetted to early endosomes in increased amounts. These findings, coupled with evidence for the increased mobilization of regulatory proteins of endocytosis, imply a strong upregulation of the EP in Alzheimer's disease.

Greater than 90% of all AD cases are sporadic. Currently there is no suitable animal model for sporadic AD. The early appearance of EP abnormalities and the specificity of these abnomralities in SAD patients suggest that these abnormalities reflect an important pathologic mechanism relevant to the most common form of AD, particularly the β-amyloidogenesis in SAD, the mechanism of which is currently unknown. Thus, there is a need for cellular or animal models of this increased activity, both for increasing the understanding of the pathophysiology underlying AD, and for use in assaying drugs for their use in treating or preventing AD.

Despite the extensive study of AD, the pathogenetic significance of the upregulation of the EP remains unclear. Thus, there is also a long-sought need to understand the importance of increased endocytosis and lysosomal activity in AD.

SUMMARY OF THE INVENTION

In human SAD and Down's syndrome (DS) brains, the total endosomal volume per neuron is 3-fold larger, on average, than in normal control values. Enlarged endosomes are seen in some cortical neurons in infants and third trimester fetuses with DS decades before extracellular β-amyloid deposition is detectable. Similarly, in early stage SAD, endocytic alterations are the earliest cellular change observed in neurons and are present before clinical symptoms are evident and before substantial β-amyloid is deposited.

Our finding of intracellular Aβ within enlarged endosomes in Down syndrome (DS) as early as late gestation suggests a strong association between EP activation and β-amyloidogenesis. Several additional lines of evidence also support the importance of the EP in the production of both forms of Aβ1, Aβ1-40 and Aβ1-42: (i) cultured cells stably transfected with wild type APP, APPswe (APP Swedish mutation or APP670/671), or APPswe/V717L (Indiana mutation), combined with deletion of the APP C-terminal endocytic targeting signal, showed a decrease in Aβ1-40 secretion and a decrease in the ratio of Aβ42/40, suggesting a decrease in Aβ42 production (Stokin et al., 6th Int'l. Conf. on Alzheimer's disease, Amsterdam, 1998); (ii) the expression of the dominant negative dynamin mutant, which prevents endocytosis, showed decreased ratios of secreted Aβ1-42/Aβ1-40 for the three foregoing APP-expressing cell lines (Stokin et al., 6th Int'l. Conf. on Alzheimer's disease, Amsterdam, 1998); and (iii) cell models using chimeric forms of APP that were retained in the ER, were directed to the lysosome, or to the cell surface showed that Aβ1-40 was produced mainly in the EP, and that Aβ1-42 was produced both in the endoplasmic reticulum/cis-Golgi apparatus and in the EP (Soriano et al., 6th Int'l. Conf. on Alzheimer's disease, Amsterdam, 1998; Soriano et al., J. Biol. Chem. 274:32295–32300, 1999).

We hypothesize that the endocytic pathway abnormalities that alter APP processing and lead to the increased production of Aβ in SAD and DS are accentuated by the APOE ε4 allele, implying mechanistic links among EP alterations, β-amyloidogenesis, and genetic susceptibility for AD. Activation of neuronal endocytosis is not a consequence of Aβ overproduction or β-amyloid deposition, as we have not detected EP abnormalities in individuals with FAD caused by PS mutations that exhibit abundant β-amyloid deposition. Using compartment-specific markers to identify early endosomes (rab5) combined with markers of endosomal fusion (rabaptin 5, early endosomal antigen EEA 1) and recycling (rab4), we have shown an upregulation of both endosomal fusion and recycling, indicating increased EP activation.

Accordingly, the invention features methods for identifying compounds for the treatment of AD.

In a first aspect, the invention features a method for identifying a candidate compound as a compound that is useful for the treatment of AD that includes: a) providing a Tn65Dn mouse; b) administering the candidate compound to the mouse; and c) measuring the abnormal activity of the EP and/or a change in AP generation. A decrease in the EP activity compared to the activity in a control Tn65Dn mouse not contacted with the candidate compound identifies the candidate compound as a compound that is useful for the treatment of AD. Similarly, a decrease in Aβ generation in a mouse, relative to a mouse not contacted with the candidate compound, also identifies a compound as one that is useful for the treatment of AD.

In a second aspect, the invention features a method for identifying a candidate compound as a compound that is useful for the treatment of AD. The method includes: a) providing a cell from a Tn65Dn mouse; b) contacting the cell with the candidate compound; and c) measuring the abnormal activity of the EP, wherein a decrease in the EP activity, compared to the activity in a control cell (also from a Tn65Dn mouse) not contacted with the candidate compound, identifies the candidate compound as a compound that is useful for the treatment of AD. As described above, Aβ generation can also be used as a measurement; a decrease in Aβ generation in a cell mouse, relative to the control cell, also identifies a compound as one that is useful for the treatment of AD. In preferred embodiments, the cell is from a cell line derived from the mouse. A preferred cell line includes a fibroblast cell line, a neuronal cell line, or a neuroblastoma cell line. In related embodiments, the cell is a fibroblast, a neuron, or an endothelial cell.

In a third aspect, the invention features a method for identifying a candidate compound as a compound that is useful for the treatment of AD. The method includes: a) providing a cell expressing a recombinant nucleic acid that causes abnormal activity of the endocytic pathway; b) contacting the cell with the candidate compound; and c) measuring the activity of the EP or Aβ generation activity, wherein a decrease in the abnormal activity, relative to the activity in a control cell expressing the recombinant nucleic acid but not contacted with the candidate compound, identifies the candidate compound as a compound that is useful for the treatment of AD.

In preferred embodiments, the recombinant nucleic acid includes rab5, 46 kDa mannose 6-phosphate receptor (MPR46), cathespin (Cat D), or nucleic acids encoding other lysosomal hydrolases trafficked by the mannose 6-phosphate tag. In various embodiments, the cell is from a fibroblast cell line, a neuronal cell line, or a neuroblastoma cell line or is a fibroblast, a neuron, or an endothelial cell.

In preferred embodiments of the second and third aspects, the cell is in an animal, or the cell is in vitro.

In a fourth aspect, the invention features a method for identifying a candidate compound as a compound that is useful for the treatment of AD. The method includes a) providing a mouse expressing a transgene that results in increased activity of the EP; b) administering the candidate compound to the mouse; and c) measuring the activity of the EP or Aβ formation activity, wherein a change in the abnormal activity, relative to the activity in a mouse expressing the transgene but not contacted with the candidate compound, identifies the candidate compound as a compound that is useful for the treatment of Alzheimer's disease.

In a preferred embodiment, the recombinant nucleic acid includes rab5, MPR46, Cat D, or other lysosomal hydrolases trafficked by the mannose 6-phosphate tag.

In preferred embodiments of the first, second, third, and fourth aspects, the abnormal activity includes increased endosomal fusion, increased endosomal recycling, upregulation of MPR46, accumulation of lysosomal hydrolases in early endosomes, or accumulation of Aβ in early endosomes.

In a fifth aspect, the invention features a method for identifying a candidate compound as a compound that is useful for the treatment of Alzheimer's disease. This method includes the steps of: (a) providing a non-human animal; (b) administering to the animal a compound that induces lysosomal dysfunction; (c) administering to the animal a candidate compound; and (d) measuring neurodegeneration in the animal. A decrease in neurodegeneration, relative to an animal administered the compound that induces lysosomal dysfunction but not the candidate compound, identifies the candidate compound as a compound that is useful for the treatment of Alzheimer's disease. Preferably, the animal is a Tn65Dn mouse or a mouse expressing a transgene comprising a recombinant nucleic acid that increases activity of the endocytic pathway (such as the ones described herein).

In various embodiments, the compound that induces lysosomal dysfunction is a lysosomal protease inhibitor, the animal has increased endocytic pathway activity relative to a normal animal.

By "abnormal activity of the endocytic pathway" is meant an activity that is normally not observed in a control cell or animal. Abnormal activities of the EP include: (i) increased endocytic rates; (ii) increased endosomal fusion and recycling; (iii) accumulation of lysosomal hydrolases in early endosomes; (iv) increased activity of lysosomal hydrolase in early endosomes; (v) upregulation of MPR46; and (vi) accumulation of β-amyloidogenic fragments in early endosomes.

A compound that "decreases" or "reduces" the abnormal activity of the endocytic pathway is one that exhibits any diminution in one or more of the foregoing activities. The decrease in abnormal activity is preferably by at least 5%, more preferably by at least 10%, and most preferably by at least 25%, 50% or more. The percent change is usually measured for a period of hours or days, but can be measure in terms of weeks or even longer.

By "lysosomal dysfunction" is meant an alteration in one function of the lysosomal system. The alteration is preferably by at least 5%, more preferably by at least 10%, and most preferably by at least 25%, 50% or more.

The invention provides methods for identifying drugs useful for the treatment or prevention of AD. Additionally, the invention provides new drug targets for rational drug design.

Other features and advantages of the invention will be apparent from the following description of the preferred embodiments thereof and from the claims.

BRIEF DESCRIPTION OF THE DRAWINGS

FIG. 8B).

DETAILED DESCRIPTION OF THE INVENTION

We have discovered that early endosomal abnormalities in SAD precede significant β-amyloid deposition and neurofibrillary pathology and that it is very likely that these abnormalities lead to the resulting neuropathology in at least SAD patients. We have further discovered that these endosomal abnormalities can be mimicked in cell or animal models by either increasing endocytosis or by altering trafficking in the EP in transgenic mice or transformed cell lines. Finally, we have found that the segmental trisomy 16 mouse, Ts65Dn, previously discounted as a suitable mouse model of AD, displays the early hallmarks of endosomal abnormalities.

Each of the transgenic mice and transformed cell lines serve as models for understanding the cell biology underlying AD, as well as for testing candidate drugs for their efficacy and safety in the treatment of this prevalent disease.

EXAMPLE 1

Figure 1:
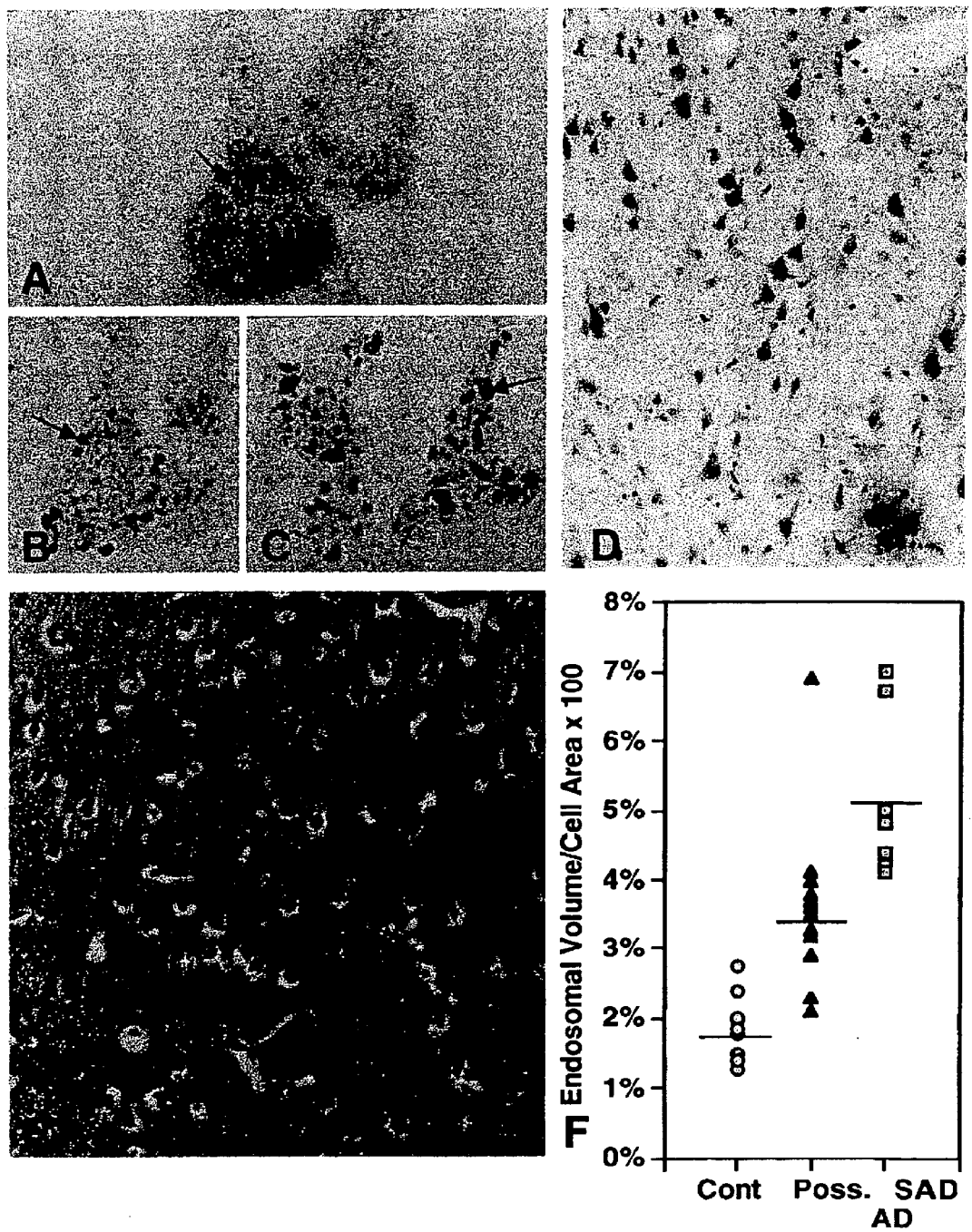
FIGS. 1A-1C are a series of photographs of tissue sections of prefrontal cortex of a control (FIG. 1A) and two early stage AD cases (FIGS. 1B and 1C) labeled with anti-rab5 antibody.
FIGS. 1D and 1E are photographs of adjacent tissue sections of prefrontal cortex from an early stage AD case processed for Aβ immunohistochemistry (FIG. 1D) or stained by Bielschowsky stain (FIG. 1E).
FIG. 1F is a graph showing that the average endosomal volume per neuron in the early stage AD cases was elevated compared to that of normal controls (control mean, 1.88%; possible AD mean, 3.68%; SAD mean, 5.04%).

Endosomal Abnormalities Precede β-amyloid Deposition and Early Neurofibrillary Change We studied SAD cases that met the CERAD criteria of "possible AD," with neuropathology limited to the entorhinal cortex/hippocampus. Abnormally large endosomes were prominent not only in neurons of the entorhinal cortex, and CA2 and CA3 of the hippocampus, but also in laminae III and V of the prefrontal cortex (FIG. 1), where deposits of β-amyloid were scarce and neurofibrillary pathology was negligible by immunostaining for early tau abnormalities. These results suggested that endosomal abnormalities are the earliest cellular disturbance yet to be identified in possible AD, preceding all but the first traces of β-amyloid deposition. Studies of DS suggest that early endosomal changes can be demonstrated even earlier when individuals can be identified who are destined to develop AD. These changes could be identified before any trace of β-amyloid was present.

Abnormal activity of the EP distinguish SAD and DS from FAD caused by PS mutations. Pyramidal neurons in individuals with moderate to severe AD caused by PS1 mutations do not display the early endosomal abnormalities seen in SAD, late onset FAD-APOE ε4, DS, or APP 717 mutations. Because PS-FAD is associated with high levels of β-amyloid deposition, these results suggest that endosomal alterations are not a consequence of β-amyloid accumulation. That PS mutations do not alter endosomal function is consistent with the hypothesis that AD caused by PS1 mutations may occur via secretory pathway organelles (e.g., endoplasmic reticulum and the Golgi apparatus) rather than the EP. In contrast to EP alterations, LS activation is accentuated in PS-FAD, including in neuronal populations that are less vulnerable in SAD (e.g., laminae II and IV of prefrontal cortex).

Figure 2:
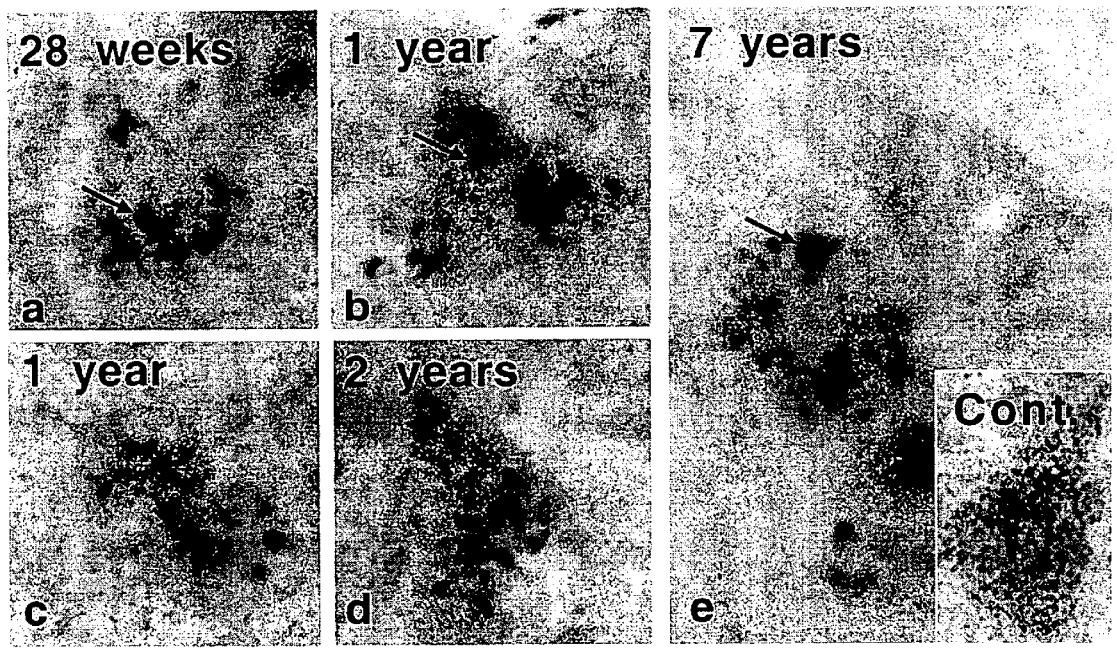
FIGS. 2A-2E are a series of photographs of tissue sections of prefrontal cortices from a fetus (FIG. 2A), infant (FIGS. 2B-2D), or young child (FIG. 2E) with DS immunolabeled for rab5.

Most individuals with DS develop neuropathological features indistinguishable from SAD at an early age. Using specific probes for early endosomes and proteins involved in the regulation of endosomal fusion (rab5, rabaptin 5, and EEA 1), we found that, like SAD, neurons from adult DS brains exhibited abnormally large early endosomes. Similarly, in tissue obtained from seven cases of fetal, infant and young DS brains, ranging in age from 28 weeks gestation to 12 years, we observed that swollen endosomal profiles greater than 1 $\mu m^3$ and similar to those seen in adult DS were present in many pyramidal neurons (FIG. 2). No detectable β-amyloid or abnormal neurofibrillary changes were seen in the brain parenchyma of the young DS brains. We observed that intraneuronal Aβ colocalized with enlarged endosomes of infant DS less than 1 year of age, consistent with the observations of Teller et al. (Nature Med. 2: 93–95, 1996), who showed increased Aβ 1-42 levels in fetal DS brains as early as 21 weeks gestation.

Given that endosomes are potentially a major site of Aβ production, the presence of atypically large early endosomal profiles suggests that Aβ production in early endosomes may be accelerated in SAD long before it accumulates extracellularly. If so, other factors such as alterations in Aβ clearance are likely to be needed to promote β-amyloid deposition.

Figure 3:
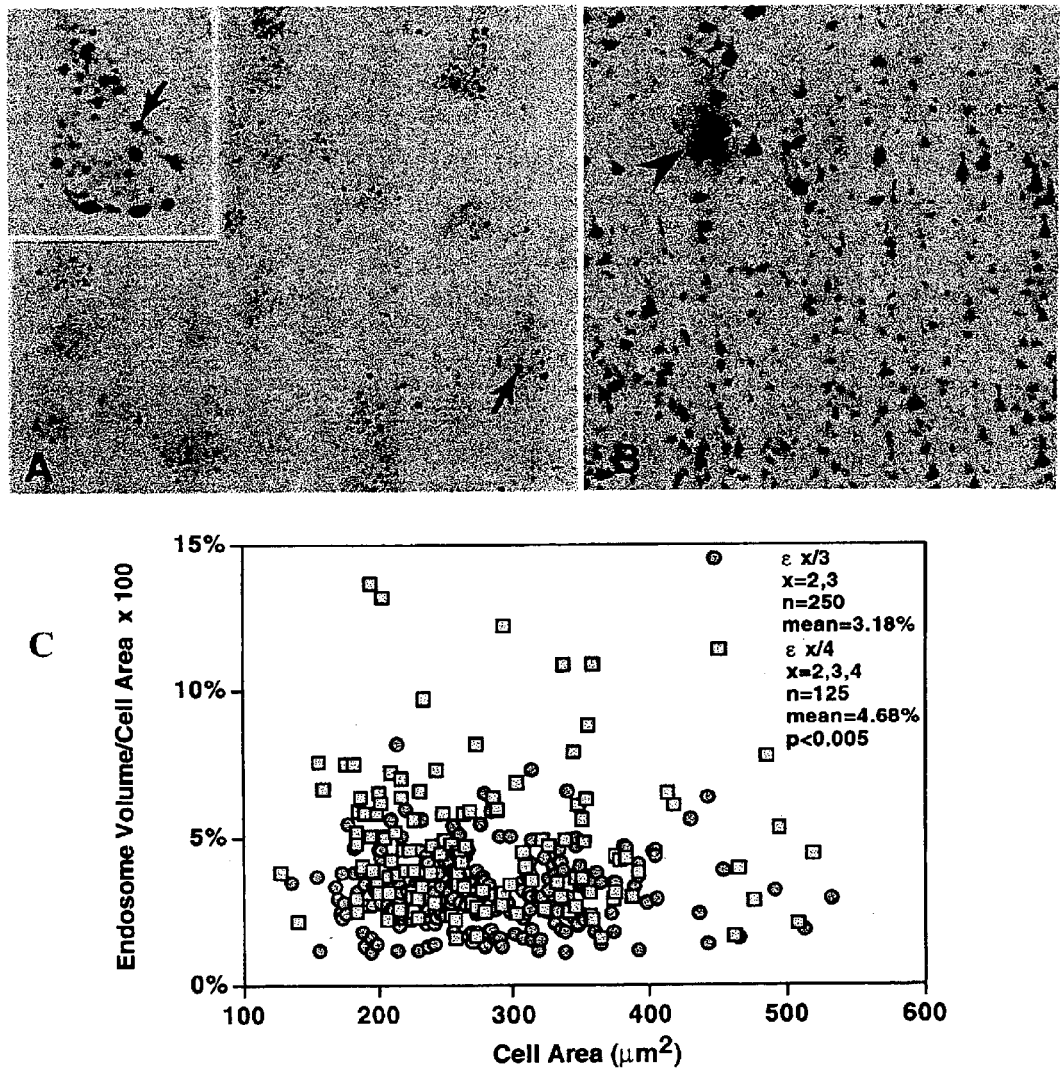
FIGS. 3A and 3B are a series of photographs of tissue sections of the prefrontal cortex from early stage AD brains carrying the APOE ε4 genotype immunolabeled for rab5.
FIG. 3C is a schematic illustration showing that the endosomal volume per neuron was 50% higher in individuals carrying one or both copies of APOE ε4.
Figure 4:
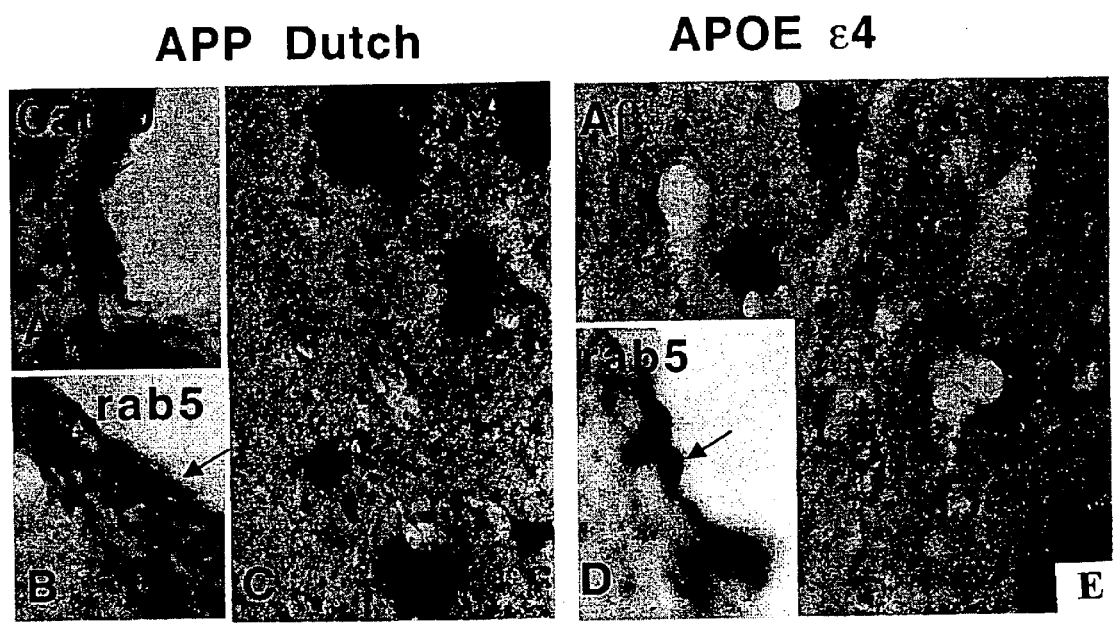
FIGS. 4A-4E are a series of photographs showing early endosomal abnormalities in the cerebral vascular epithelium in heritable Dutch CAA (FIGS. 4A-4C) and late onset FAD carrying the APOE ε4 allele (FIG. 4B).

EXAMPLE 2
Accentuation of Early Endosomal Abnormalities in Individuals Carrying the APOEε4 Allelle We examined tissue sections from a total of 15 early stage cases, consisting of 10 cases with APOE ε3 or APOE ε2 alleles and 5 cases carrying one or both copies of the APOE ε4 allele. These brains exhibited minimal histopathology and met the CERAD criteria of "possible AD." Neocortical sections were immunostained with rab5 antiserum and morphometric analyses were performed on groups of 25 neurons per brain. We found that the average mean endosomal volume/neuron in the early stage cases with the ε4 alleles was 50% larger than the AD cases with the ε3 or ε2 alleles (FIG. 3), suggesting a link between EP alterations and inheritance of the APOE genotype. Altered endocytosis would be expected to influence ApoE internalization and function, a prediction consistent with the observation of elevated ApoE immunoreactivity in pyramidal neurons in AD.

EXAMPLE 3
Transfected Cell Models of Endosomal and Hydrolase Trafficking Abnormalities in AD Brain We produced fibroblast cell lines that have been genetically engineered to model the enlargement of early endosomes, increased endocytosis, and increased trafficking of proteases to early endosomes that we have observed in AD brain. We believe that this strategy of mimicking pathological changes in the EP known to occur in AD brain has advantages over currently used manipulations of APP trafficking that may not be representative of disease-relevant mechanisms.

MPR46

Figure 5:
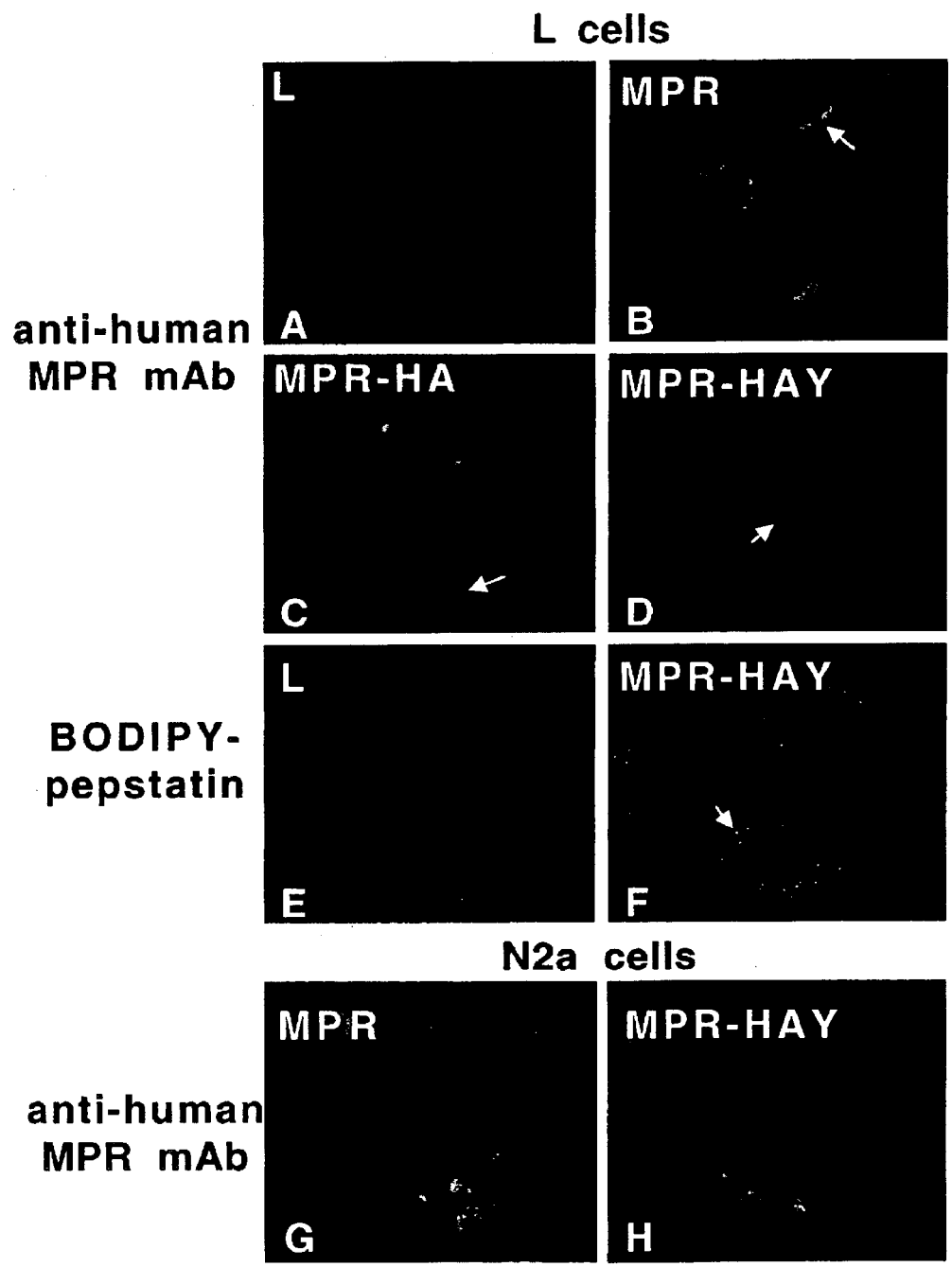
FIGS. 5A-5D are a series of photographs of immunofluorescence labeling of human MPR46 in control murine L cells (FIG. 5A), or L cells stably-transfected with human MPR46 (FIG. 5B), MPR-HA (FIG. 5C), or MPR-HAY (FIG. 5D).
FIGS. 5E and 5F are photographs of control L cells (FIG. 5E) or L cells stably-transfected with MPR-HAY (FIG. 5F) showing that MPR-HAY-transfected cells preferentially took up BODIPY-pepstatin from the medium.
FIGS. 5G and 5H are photographs of immunofluorescence labeling of human MPR in N2a cells expressing MPR46 (FIG. 5G) or MPR-HAY (FIG. 5H).
FIG. 5I is a schematic illustration showing overexpression of MPR46 or a MPR46 trafficking mutant results in increased Aβ levels in the culture medium in cells overexpressing human APP.
FIG. 5J is a schematic illustration showing overexpression of MPR46 trafficking mutant results in increased Aβ levels in the culture media of cells that are not overexpressing APP.

To mimic the hydrolase mistrafficking seen in AD, we isolated a cDNA encoding the human MPR46 and expressed this in stably transfected murine fibroblast-like cell lines (L cell; FIG. 5). In addition, we constructed two targeting mutants of MPR46 by replacing its C-terminal tail with that of the plasma membrane influenza virus hemagglutinin (MPR-HA) or a modified HA tail containing a tyrosine-residue endocytosis motif (MPR-HAY; Roth et al., J. Cell Biol. 102:1271–1283). The wild-type MPR46 predominantly localized to perinuclear vesicles consistent with the trans-Golgi sacs and late endosomes. (FIG. 5). As predicted, MPR-HA was expressed at the cell surface, while MPR-HAY was localized primarily to small vesicles, which we have shown to be early endosomes by both rab5 immunolabeling and transferrin uptake. Using a fluorescent-tagged pepstatin, an inhibitor of Cat D that binds to the proteolytically active enzyme, we demonstrated that expression of the MPR-HAY chimera partially distributes this lysosomal hydrolase to early endosomes (FIG. 5). Overexpression of wild-type MPR46 appears to similarly redistribute Cat D to early endosomes, although to a lesser extent. Thus, by expressing MPR-HAY and/or overexpressing MPR46, we can model the increase of active lysosomal hydrolases in early endosomes seen in SAD.

Figure 5I:
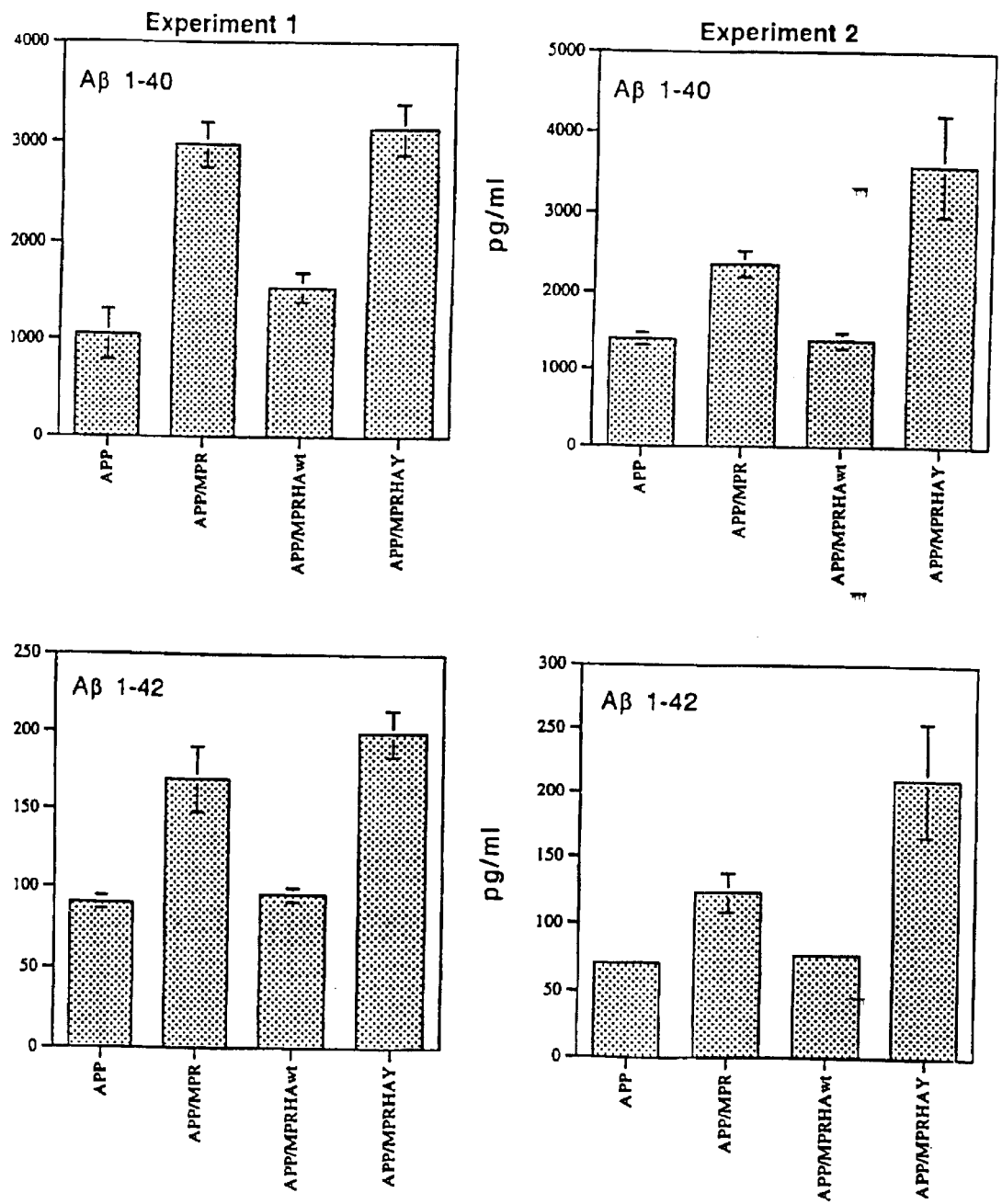
Figure 5J:
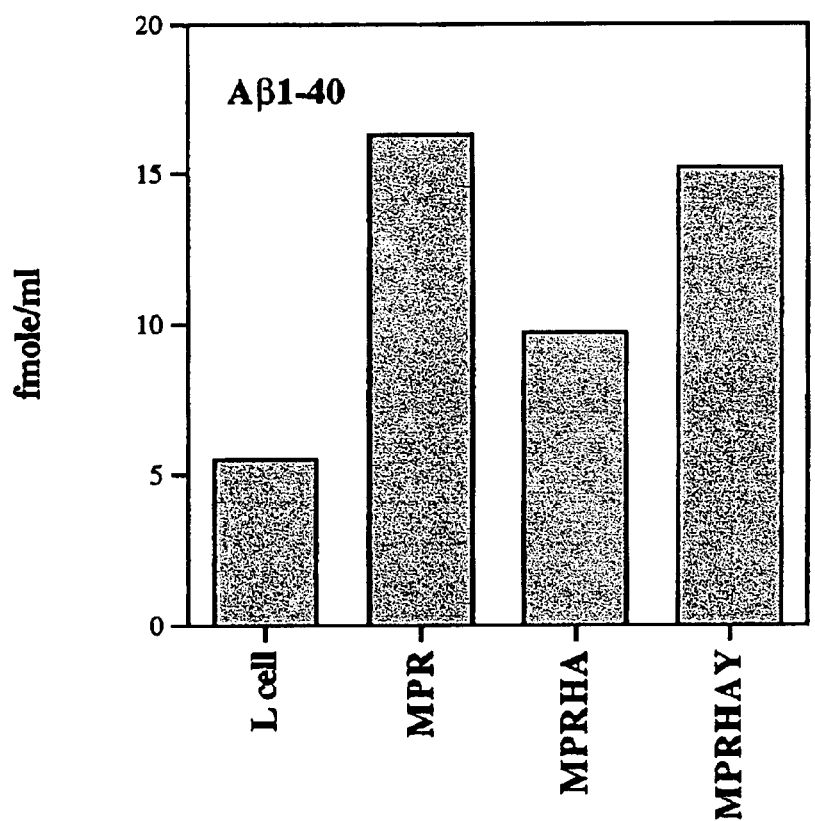
Figure 6:
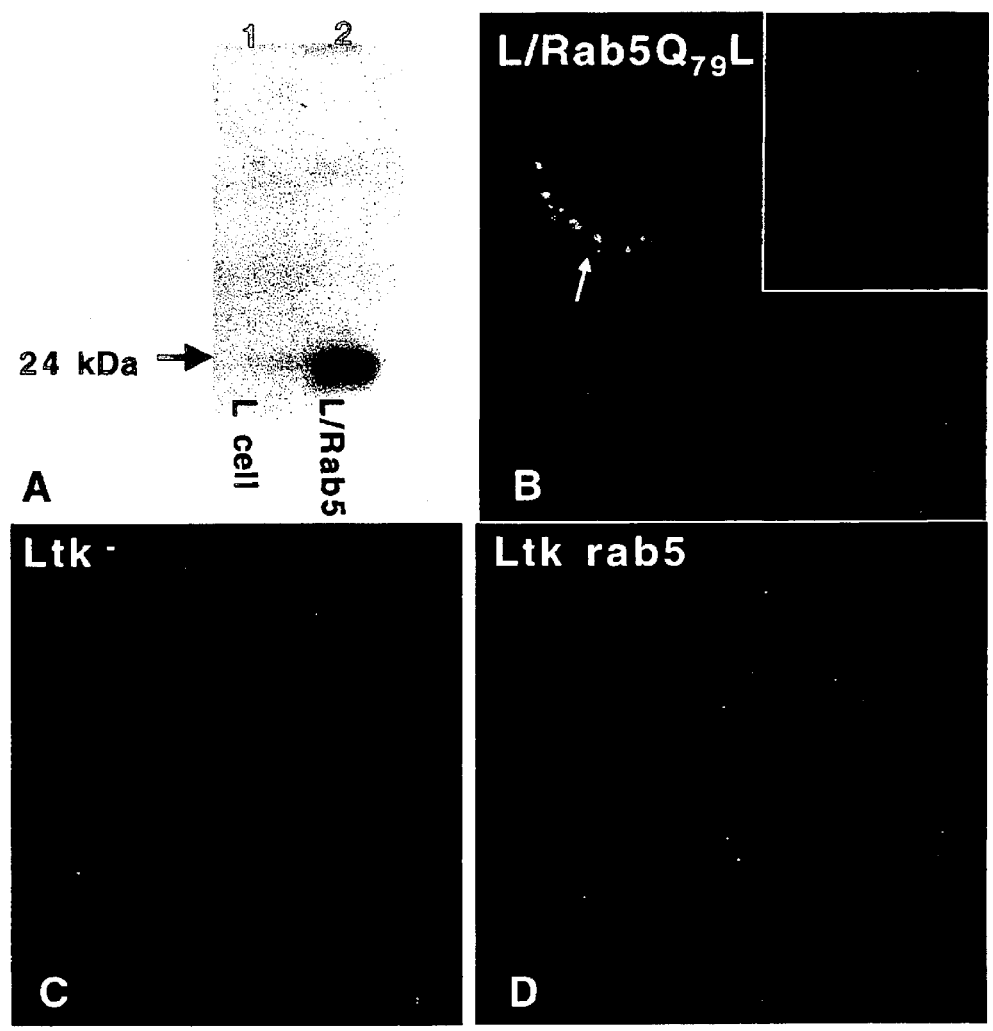
FIG. 6A is a photograph of a Western blot showing rab5 immunoreactivity in control L cells and L cells stably-transfected with rab5.
FIG. 6B is a photograph of L cells stably-transfected with rab5$Q_{79}L$ showing enlarged endosomes (arrow).
FIGS. 6C and 6D are photographs of control L cells (FIG. 6C) or L cells overexpressing wild-type rab5 (FIG. 6D) showing increased internalization of Cy3-labeled transferrin.

We introduced these constructs into L cells overexpressing wild-type human APP to determine the effect of increased hydrolases in early endosomes on APP processing. A murine L cell line overexpressing APP was transfected with MPR46 (APP/MPR), a plasma membrane-targeted MPR46 (APP/MPRHAwt), or a MPR46 construct that is preferentially trafficked to the early endosome (APP/MPRHAY). Cells were incubated for 8 hours following a media change, and the amount of Aβ1-40 and Aβ1-42 secreted into the medium during this time were determined by ELISA. Overexpression of MPR46 increased Aβ1-40 and Aβ1-42 generation above control (APP) cells (FIG. 5I). As we predicted, expression of the plasma membrane-targeted MPRHAwt construct did not affect Aβ generation. Expression of the early endosome-trafficked MPRHAY, however, increased Aβ1-40 and Aβ1-42 production over control and, in one experiment, beyond the increase seen with MPR46 expression (FIG. 5I). We confirmed these results in L cells that were not overexpressing APP. As seen in APP overexpressing L cells, overexpression of MPR46 increased the amount of endogenous mouse Aβ1-40 approximately three times above control cells (FIG. 5J). While in this experiment MPRHAwt had a small effect on Aβ1-40 production, MPRHAY expression had a much larger effect, similar to MPR46 overexpression (FIG. 5J). It is likely, based on these findings, that the redistribution of lysosomal hydrolases in human AD resulting from increased expression of MPR46 is likely to contribute to increased Aβ production. Thus, use of MPR46 and MPR46 trafficking mutants to mistraffick hydrolases provides a model for these changes in vitro and in vivo.

rab5

To model the enlargement of early endosomes and increased endocytosis seen in AD, we made stably transfected cell lines overexpressing rab5 (FIG. 5). Immunolabeling for rab5 showed enlarged endosomes, similar to those seen in neurons from individuals with SAD, when compared to non-transfected cells. In addition, we also constructed a cDNA encoding the GTP-hydrolysis deficient rab5 mutant $Q_{79}L$ (Stenmark et al., EMBO J. 13: 1287–1296, 1994) and expressed this in L cells. Expression of the rab5 $Q_{79}L$ mutant results in increased endocytosis and the fusion of early endosomes into large vacuoles. Confirming that rab5 overexpression led to abnormal activity of the EP, we demonstrated both increased uptake of fluid phase markers (FITC-dextran) and increased receptor mediated endocytosis (transferrin).

The ability of a compound to counteract the effect of rab5 overexpression and rab5$Q_{79}L$ expression on endocytosis is determined, for example, by immunolabeling using antibodies to rab5, EEA 1, and/or rabaptin 5, followed by computerized morphometric analysis. Functional uptake studies can also be used to assess fluid phase and receptor mediated endocytosis. Redistribution of hydrolases, specifically to early endosomes by MPR46 and/or MPR-HAY, are determined with assays such as immunolabeling, BODIPY-pepstatin uptake, or metabolic labeling followed by immunoprecipitation of specific lysosomal hydrolases. Administration of a candidate compound to neuroblastoma cells overexpressing MPR46 or rab5, or expressing the MPR chimeras, can also be assayed by directly evaluating APP processing or Aβ production under conditions of increased endocytic uptake or increased hydrolase delivery to early endosomes.

EXAMPLE 4
Transgenic Mice Models Having Endosomal and Hydrolase Trafficking Abnormalities in AD Brain Transgenic mouse lines overexpressing any of the foregoing constructs provide useful animal models for identifying drugs useful for the treatment of AD. These mice can be made using standard techniques. If desired, the expression of the transgenes can be restricted to neurons by use of a promoter such as the Thy 1.1, neuron-specific enolase, or Tα1 α-tubulin promoters. The transgenic mice described herein can be crossed with each other, with a mouse that has increased AD-like pathology, a mouse that is expressing a polypeptide that has a mutation found in a human with AD (e.g., APP, PS-1, or PS-2), or with a reporter mouse Any of the assays of abnormal activity of the EP can be performed to monitor the effectiveness of a candidate compound in decreasing the abnormal activity of the EP. The candidate compound can be directly administered to the mouse. Alternatively, cells from the mice, such as fibroblasts, endothelial cells, or neurons, can be assayed in vitro.

Figure 7A:
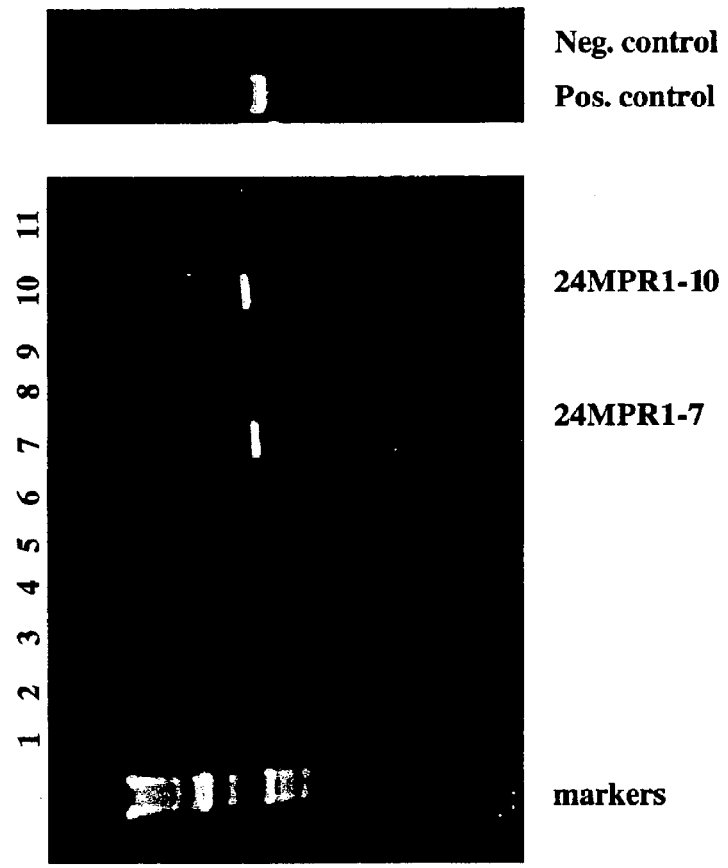
FIG. 7A is a photograph of a DNA agarose gel identifying 2 of 11 pups within a litter as carrying the Thy1.1: MPR46 transgene.
Figure 7B:
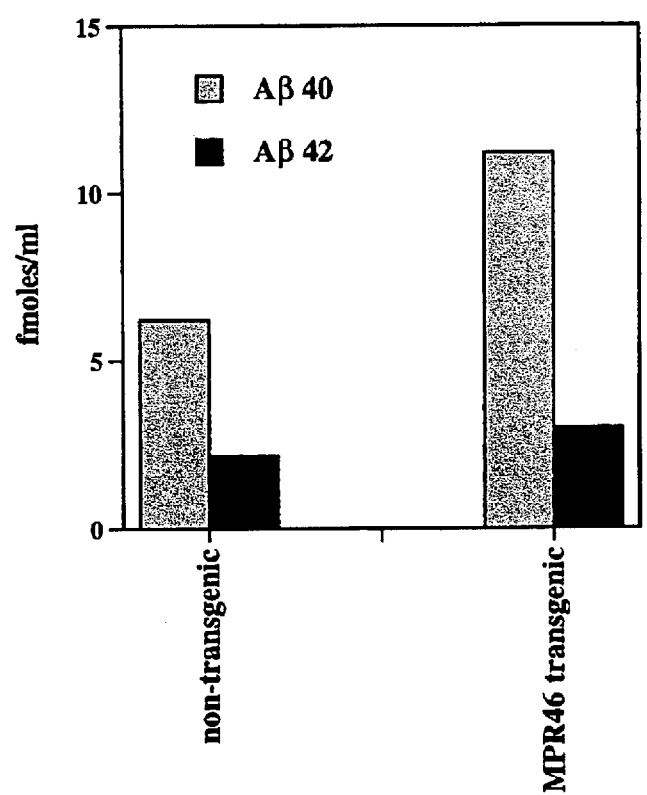
FIG. 7B is a schematic illustration showing increased Aβ levels in the brain of a transgenic mouse expressing human MPR46 under the Thy1.1 promoter.

As one example of such a transgenic mouse, we have constructed a mouse overexpressing MPR46 within neurons under the Thy-1.1 promoter. Following DNA microinjection and implantation of approximately 75 single cell embryos, 29 pups were raised to weaning. From these, two mice were identified that contained the Thy-1.1 MPR46 transgene construct. Both of these founders were shown to transmit the Thy-1.1: MPR46 transgene to F1 offspring. FIG. 7A identifies 2 of 11 F1 offspring of one such founder as carrying the Thy-1.1: MPR46 transgene. Brain Aβ levels were compared between one such F1 Thy-1.1: MPR46 transgenic mouse and a non-transgenic litter mate (FIG. 7B). While the increase in brain Aβ seen in this four week old heterozygous Thy-1.1 MPR46 transgenic mouse was modest (approximately 1.7 times of Aβ1-40), it is likely that an older mouse will show an even greater increase in Aβ. Additionally, a greater effect is likely to be seen in homozygous transgenic mouse; finally, additional transgenic lines can be generated with higher levels of MPR46 expression.

Thy-1.1: MPR46 Transgenic Mouse Methods

Neuron specific expression of human MPR46 is driven by the Thy-1.1 promoter, which has been used successfully in mice transgenic for mutant APP that show amyloid plaque deposition (Sturchler-Pierrat et al., Proc. Natl. Acad. Sci. USA 94:13287–13292, 1997). The Thy-1.1 promoter is valuable in that high levels of transgene expression have been obtained and that expression is restricted within the CNS to neurons. An 8.2 kb EcoRI mouse genomic fragment containing the whole Thy-1.1 gene forms the core of the transgene constructs (Chang et al., Proc. Natl. Acad. Sci. USA 82:3819–3823, 1985; Gundersen et al., Gene 113:207–214, 1992; Luthi et al., J. Neurosci. 17:4688–4699, 1997). After preparation by standard methods, plasmid was digested with the appropriate restriction enzymes to remove vector sequences, isolated by agarose-gel electrophoresis, and further purified by dialysis in ultra-pure water. Single cell embryos obtained from C57BL6×CBA/2 F1 hybrids were used for injection. Founder transgenic mice were identified and transgene copy number estimated by Southern blot analysis of restriction digested tail DNA using hybridization to a fragment unique to the transgene. Progeny were screened by PCR using human-specific primers. Some F1 progeny from the two transmitting founders were examined at 4 weeks of age.

EXAMPLE 5
Fibroblasts from DS Mice Exhibit Abnormal Activity of the Endocytic Pathway Explants of minced skin tissue taken antemortem from the forearm of two donors, aged five years and thirteen months, with the typical features of DS (Trisomy 21; karyotype 47, XY, +21) and from minced umbilical cord tissue of a therapeutically aborted fetus of twenty-two weeks gestation (karyotype 47, XY, +21) were grown to confluency on glass coverstips and fixed for morphologic inspection of early endosomal compartments and localization of the Aβ peptide. In each of the cell lines from the DS cases, we observed intracellular localization of Aβ in compartments close to the cell surface that were consistent with early endosomes. Thus, the abnormal activity of the EP observed in SAD and DS brains are mimicked by cultured fibroblasts from DS individuals. This finding indicates that DS fibroblasts would be a suitable model to screen candidate compounds for their ability to prevent the earliest stages of AD.

EXAMPLE 6
Molecular Analysis of Early Endosomal Abnormalities in Ts65Dn Mice

Figure 8:
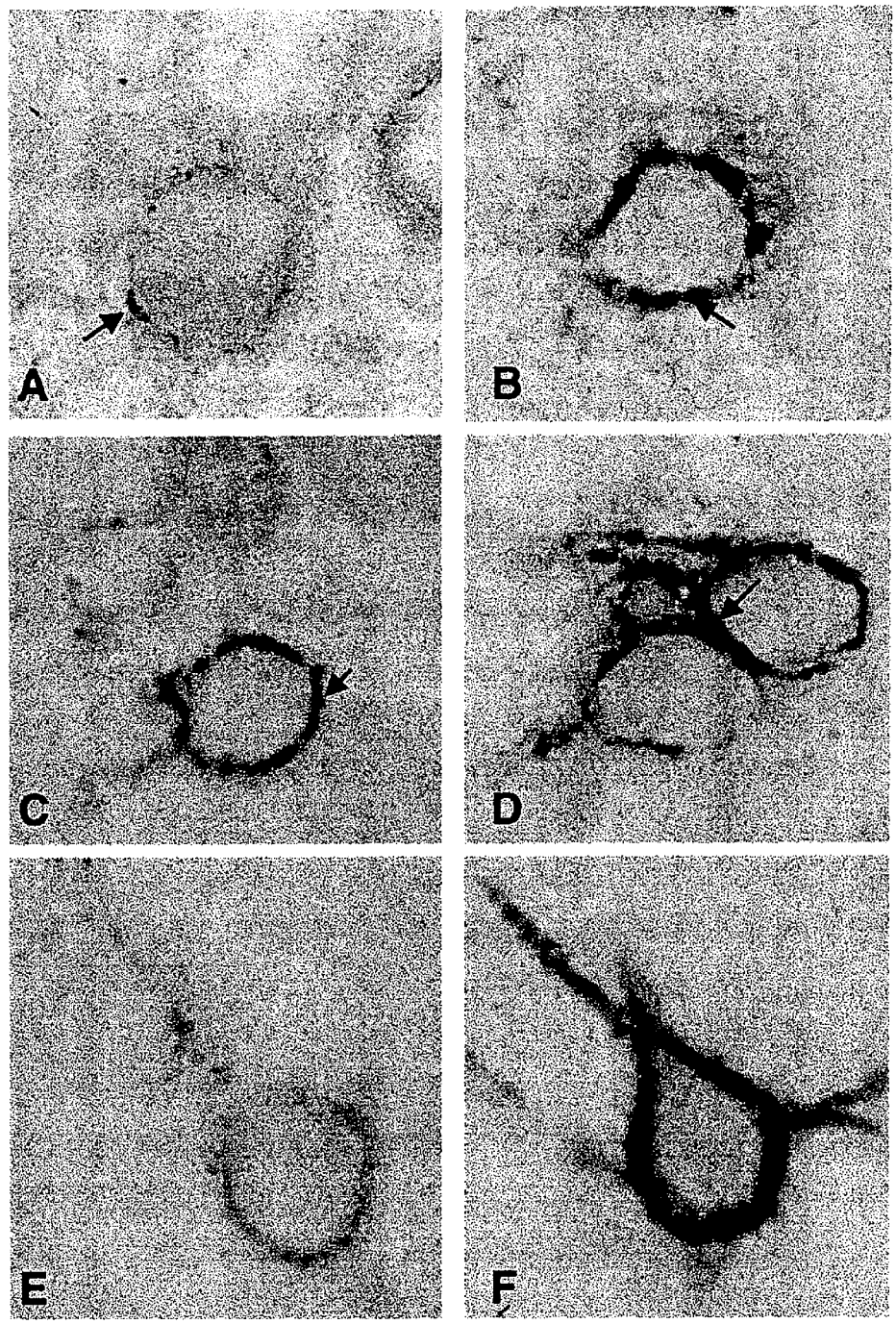
FIGS. 8A and 8B are photographs showing rab5 immunoreactivity in cortical neurons from control mice (FIG. 8A) and mice with segmental trisomy 16 (Ts65Dn.
FIGS. 8C-8F are photographs showing rab5 immunoreactivity in cortical neurons, particularly showing more labeling in Ts65Dn mice (FIG. 8F) compared to control mice (FIG. 8E).

Using mice with segmental trisomy 16 (Ts65Dn), an established in vivo model of human "translocation" DS (Holtzman et al., Proc. Natl. Acad. Sci. USA 93:13333–13338, 1996), we found that, at two months of age and prior to the appearance of any neuropathological alterations, many neurons in the neocortex and basal forebrain contained enlarged early endosomes similar to those seen in AD and DS brain (FIG. 8). At six months of age, the endosomal alterations were present within the majority of neurons in the neocortex and basal forebrain and in a substantial number of hippocampal neurons. The abnormal activity of the EP in the Ts65Dn animals is similar to that seen in human SAD and DS.

Figure 9:
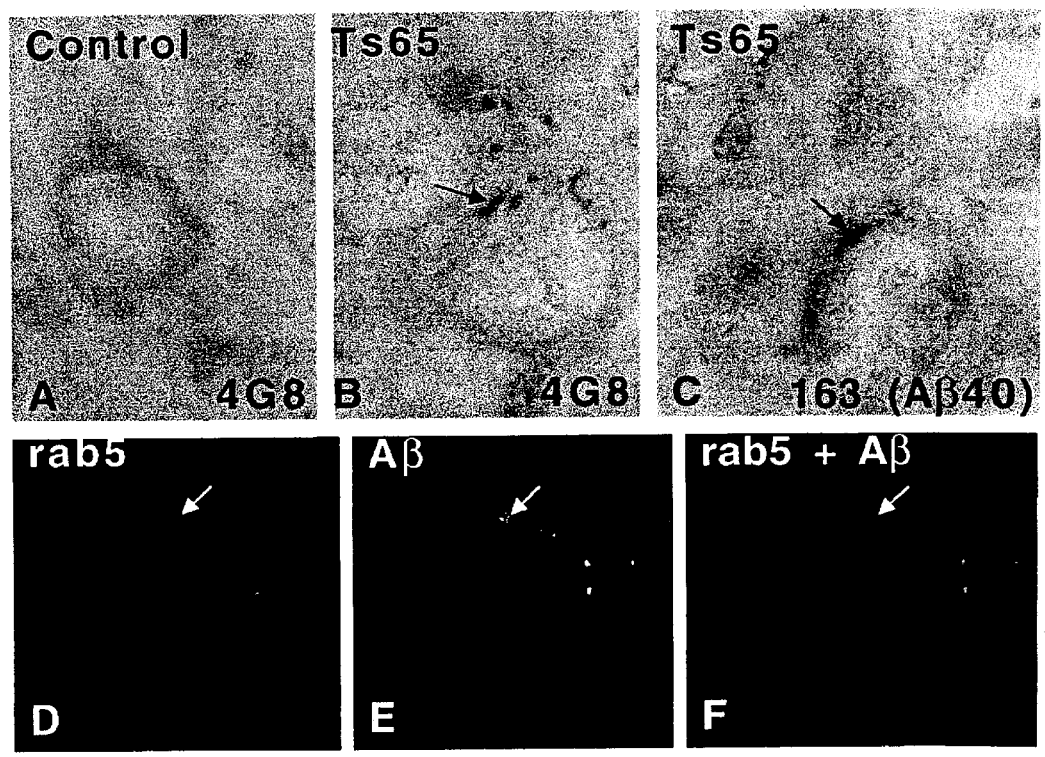
FIGS. 9A-C are photographs showing intracellular Aβ only in neurons of Ts65 mice using antibody 4G8 (FIG. 9B) and an Aβ40 specific antibody (FIG. 9C) but not in neurons of a control mouse (FIG. 9A).
FIGS. 9D-F are photographs of immunofluorescence labeling showing the coincidence (FIG. 9F) of rab5 (FIG. 9D) and Aβ (FIG. 9E) in Ts65Dn neurons.

We found in Ts65Dn mice increased neuronal content of APP and the presence of intraneuronal Aβ within vesicular compartments (FIG. 9). An antibody directed to the 17–24 region of the Aβ peptide was used to probe brain tissue from the Ts65Dn mouse (FIG. 9B), as well as postmortem brain tissue from the neocortex of cases of human fetal, infant, and young DS, and cases obtained from adult patients in the very early stages of AD.

Figure 10:
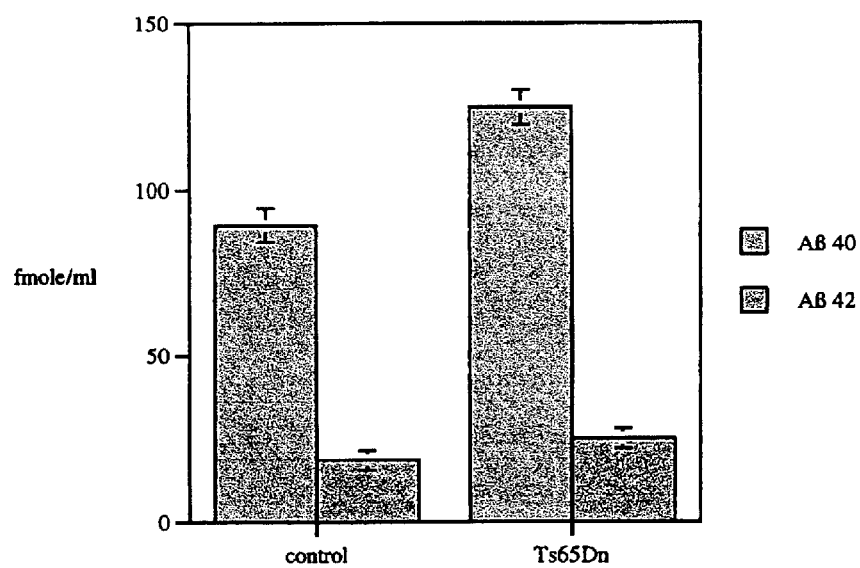
FIG. 10 is a schematic illustration showing increased levels of Aβ in the brains of Ts65Dn mice vs. control mice.

Using immunocytochemical techniques and light or confocal microscopy, we found the presence of small and discrete deposits of anti-Aβ immunoreactive material within neurons of the Ts65Dn mice (FIGS. 9D-F), the early stage DS cases, and the cases in the earliest stages of AD. None of the Ts65DN mice, the early stage DS cases, or the early stage AD cases displayed evidence of extracellular β-amyloid protein in those same brain regions where intracellular Aβ was detected. Additionally, we have seen an increase in Aβ detected by sandwich ELISA in homoguates prepared from Ts65Dn mouse brain vs. control mouse brain (FIG. 10). We have found both Aβ40 and Aβ42 to be increased by approximately 1.4 times.

Other similarities among the Ts65Dn mice, early DS, and early stage AD were observed. These included abnormalities in proteins associated with the regulation of the activity of the EP.

The Ts65Dn mouse can serve as a model for early stages of cellular pathology and Aβ formation seen in sporadic AD and DS that are not modeled by existing transgenic mouse models based on mutations associated with familial forms of AD in the presenilin genes and APP gene. This model is useful for assaying candidate compounds for their ability to decrease the foregoing abnormalities and to decrease intracellular production of Aβ. Additionally, standard mouse learning and behavior paradigms known to those skilled in the art can be used to assess brain function in Ts65Dn mice administered candidate compounds.

The Ts65Dn mouse provides other uses as an in vivo model of the EP upregulation seen in AD and DS. For example, by examining the other mice that are only partially trisomic for the human homolog of chromosome 21, we can gather additional information on the specificity of the endosomal system upregulation and begin to dissect the genes that may play an essential role. Crossing Ts65Dn mice with a mouse carrying a balanced translocation of chromosome 16, T(12;16)1Cje (Huang et al., Arch. Biochem. Biophys. 344:424–432, 1997) generates four genotypes: litter-matched normal control mice; Ts65Dn; the previously described segmental trisomy Ts1Cje (Sago et al., Proc. Natl. Acad. Sci. USA 95:6256–6261, 1998); and the poorly characterized segmental trisomy Ms1Ts65. The T(12;16)1Cje mice are phenotypically normal because the translocation is balanced. The Ts1Cje mouse is trisomic for the region of mouse chromosome 16 from the Sod1 to Mx1 genes, although the Sod1 gene is inactive (Sago et al., Proc. Natl. Acad. Sci. USA 95:6256–6261, 1998). These mice do not have an extra copy of the App gene. Ts1Cje mice have less severe learning deficits than do the Ts65Dn mice and, unlike the Ts65Dn mice, do not show degeneration of basal forebrain cholinergic neurons (BFCN) (Sago et al., Proc. Natl. Acad. Sci. USA 95:6256–6261, 1998). The Ms1Ts65 mice are trisomic for the region of mouse chromosome 16 from the App gene to, but not including, the Sod1 gene. Developmental retardation and BFCN degeneration have not been characterized in the Ms1Ts65 mouse. If Ts65Dn mice, but not Ts1Cje mice, show abnormally large endosomes, this indicates that genes in this part of the chromosome (the App to Sod1 region) are essential to the development of this defect. As the Ts1Cje mice do not show BFCN degeneration, this result would suggest that endosomal system upregulation and BFCN degeneration share a common genetic underpinning in these animals. While the App gene in this region is likely to be of importance, we suspect that a dosage-effect for APP will not fully explain the Ts65Dn endosomal system upregulation, as we have not seen abnormally large endosomes in the APPswe transgenic mice nor do APP overexpressing mice develop BFCN degeneration. Characterizing the Ms1Ts65 mice that carry an extra copy of App but lack many of the other genes over represented in Ts65Dn mice will directly complement our analysis of the other mice.

It is highly likely that crossing the Ts65Dn mice with mice expressing human APOE ε4 will enhance EP upregulation, similar to the greater neuronal EP upregulation seen in AD cases with the APOE ε4 genotype. This may be an even better model of EP abnormalities in which to study Aβ production and Aβ deposition, as well as to test candidate drugs for efficacy and safety.

We further predict that altering lysosomal function will create a better model of AD pathology, a model that will include more extensive neurodegeneration and allow us to establish a relationship between upregulation of the EP and lysosomes and neuronal atrophy. We can modulate lysosomal function by inhibiting lysosomal proteases in vivo individually or by enzyme class in any of these in vivo mouse models.

In one method, infusion pumps are implanted in animals at 8 weeks of age and the animals are sacrificed 28 days later. We can perform the following assessments: (a) determine cytochemically and biochemically whether administration of a candidate compound prevents or reduces the EP activity abnormality; (b) assess neurodegeneration in the inhibitor treated mice in the presence and absence of candidate compounds; and (c) assess any changes in β-amyloid productiondeposition.

To induce lysosomal dysfunction in vivo, the activity and/or expression of a specific cathepsin or groups of cathepsins is modified by chronic intraventricular infusion of appropriate inhibitors. In one example, proteases are inhibited in vivo in the mouse brain using an ALZET osmotic pump brain infusion kit in conjunction with model 2004 mini-osmotic pumps (0.25 mL/hr delivery rate, 28 days) (Frautschy et al., J. Neurosci. 18:8311–8321, 1998). The following inhibitors (with approximate dosages) are suitable for inducing lysosomal dysfunction: leupeptin (0.5 mmol to 4 mmol) is a broad-spectrum inhibitor of thiol proteases (e.g., Cat B, Cat L, Cat S); pepstatin (0.1 mmol to 1 mmol) inhibits Cat D, and inhibits mouse aspartyl proteases systemically at these concentrations; and Z-PAD (10 mmol to 100 mmol) inhibits thiol proteases but with greater specificity than leupeptin for Cat B and Cat L. Aprotinin (1 mmol to 30 mmol) broadly inhibits serine proteases and is principally used as a control since the major proteases in lysosomes are not of the serine type.(Green and Shaw, J. Biol. Chem. 256:1923–1928, 1981; Ohnishi et al., Cancer Res. 50:1107–1112, 1990; Umezawa, H. Academic Press, Vol. XLV, Part B, 1976; Frautschy et al., J. Neurosci. 18:8311–8321, 1998; Ivy et al., Adv. Exp. Med. Biol. 266:31–45, 1989; Ivy et al., Brain Res. 498:360–365, 1989; Kuki et al., Dementia 7:233–238, 1996; Okada et al., Neurosci. Res., 19:59–66, 1994; Bednarski et al., Exp. Neurol. 150:128–135,1998; Bednarski et al., J. Neurochem. 67:1846–1855, 1996; Bednarski et al., J. Neurosci. 17:4006–4021, 1997; Van Noorden et al., J. Rheumatol. 15:1525–1535, 1988). Doses were chosen at an anticipated effective dose and a second, higher dose. Other inhibitors are also useful for inducing lysosomal dysfunction, including, for example, vinyl sulfone inhibitors that are selective for cysteine cathepsins and have poor affinity for calpains, and peptidyl fluoromethylketone inhibitors that preferentially inhibit Cat B (Palmer et al., J. Med. Chem. 38:3193–3196, 1995; Ahmed et al., Biochem. Pharmacol. 44:1201–1207, 1992; Esser et al., Arthritis Rheum 37:236–247, 1994; Riese et al., J. Clin. Invest. 101:2351–2363, 1998).

To administer the candidate compounds in the presence or absence of inhibitor(s), eight week old mice are anesthetized with pentobarbital (40–50 mg/kg i.p.) and placed in a stereotaxic apparatus with mouse adapter (David Kopf Instruments, Tujunga, Calif.). After sacrifice, placement of the probe into the lateral ventricle is confirmed and one hemi-brain immersion-fixed and the other hemi-brain homogenized for protease assays. We determine the efficacy of the candidate compound by assaying the activity of proteases in brain homogenates (e.g., Cat B, Cat L, Cat D, and trypsin (Brunk et al., Free Radic. Biol. Med. 19:813–822, 1995; Marotta and Nixon, J. Neurochem. 43:507–516, 1984; Koshikawa et al., Am. J. Pathol.

153:937–944, 1998); see, for example, Cat D shown in FIG. 11F). Chronic inhibition (7+days) by chloroquine or leupeptin infusion results in accumulation of lipofuscin-like material in neurons while aprotinin infusion, which does not inhibit any major lysosomal protease, does not (Arai et al., Ann. Neurol. 38:649–652, 1995; Ivy et al., Adv. Exp. Med. Biol. 266: 31–45, 1989; Ivy et al., Brain Res. 498:360–365, 1989; Kuki et al., Dementia 7:233–238, 1996) (compare autofluorescence in neurons from a leupeptin treated mouse (FIG. 11B) with a vehicle treated (20mM HEPES) mouse (FIG. 11A). Lipofuscin accumulation in neurons from inhibitor treated mice is assessed by two criteria: autofluorescence emission (FIG. 11B) and EM morphological appearance. Lipofuscin granules are defined at the EM level as having a single layer of membrane and a bipartite structure consisting of electron lucent lipoid material and electron dense material (Cataldo and Nixon, Ann. N.Y. Acad. Sci. 679: 87–109, 1993).

Dysfunction of a particular protease or group of proteases may lead to a compensatory increase in levels of other lysosomal proteases (Bednarski and Lynch, Neuroreport 9:2089–2094, 1998). Analysis of the LS is performed, using assays described herein, to determine the impact of inhibitor infusion on the overall expression of most lysosomal hydrolases, hydrolases inhibited by one or more of the treatments (Cat D, Cat B), and a probe that is not affected by any of the inhibitors (LAP). In FIGS. 11C-F, increased brain levels of Cat D, a protease not directly affected by leupeptin, is shown by immunohistochemistry (FIG. 11D), Western blot analysis (FIG. 11E), and activity assay (FIG. 11F) following 4 weeks of intraventricular infusion of leupeptin. Increases in CatD are particularly relevant to models of AD because Cat D activation has been shown to lead to activation of some cell death pathways and because Cat D itself has recently been identified as a potential β-secretase (Gr üninger-Leitch et al., Nature Biotechnol. 18: 66–70, 2000).

Figure 12:
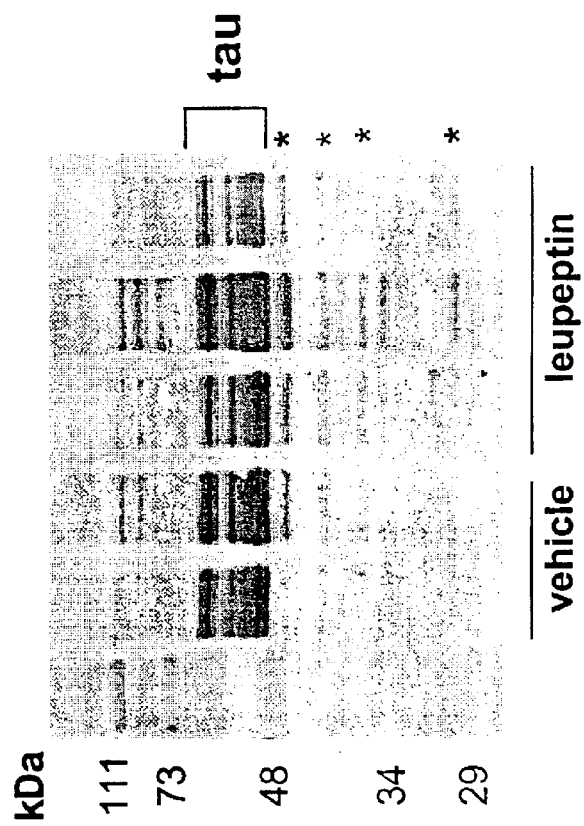
FIG. 12 is a photograph of a Western blot showing an increase in the lower molecular weight forms of tau in leupeptin-treated mice.

Several studies have recently raised the possibility that abnormal forms of tau is metabolized in lysosomes. Western blot analysis of the cytoskeletal associated protein tau in brain revealed in increase in lower molecular weight forms of the protein (Mr~30–34 kDa) in leupeptin-infused mice, suggesting an important lysosomal component to tau processing in neurons (FIG. 12). There are numerous assays for tau known in the art. For example, the processing of tau by immunocytochemistry and Western blot analysis is performed using an antibody that recognizes both phosphorylated and non-phosphorylated forms (Adamec et al., Brain Res. 757:93–101, 1997). Abnormal tau conformation and hyperphosphorylated tau is examined using suitable monoclonal antibodies. (e.g., MC1 (Jicha et al., J. Neurosci. Res. 48:128–132) and AT8 (Innogenetics, Gent, Belgium)). EM analysis can be performed to characterize cytoskeletal changes in neurons (Nixon, Bioessays 20:798–807, 1998). Alternatively, the magnitude of neurodegeneration in the mice can be determined by Nissl stain.

In addition, Aβ levels can be determined in mice administered inhibitors with or without candidate compounds. Levels of APP, APPs, APP carboxy-terminal fragments, and Aβ production can be examined using methods described herein. Additionally, the presence of Aβ in endosomal and lysosomal compartments is assayed by double-label immunocytochemistry using antibodies to Aβ and appropriate markers for these compartments (e.g., rab5).

Models of AD Neuropathology Following Leupeptin Infusion

Figure 13:
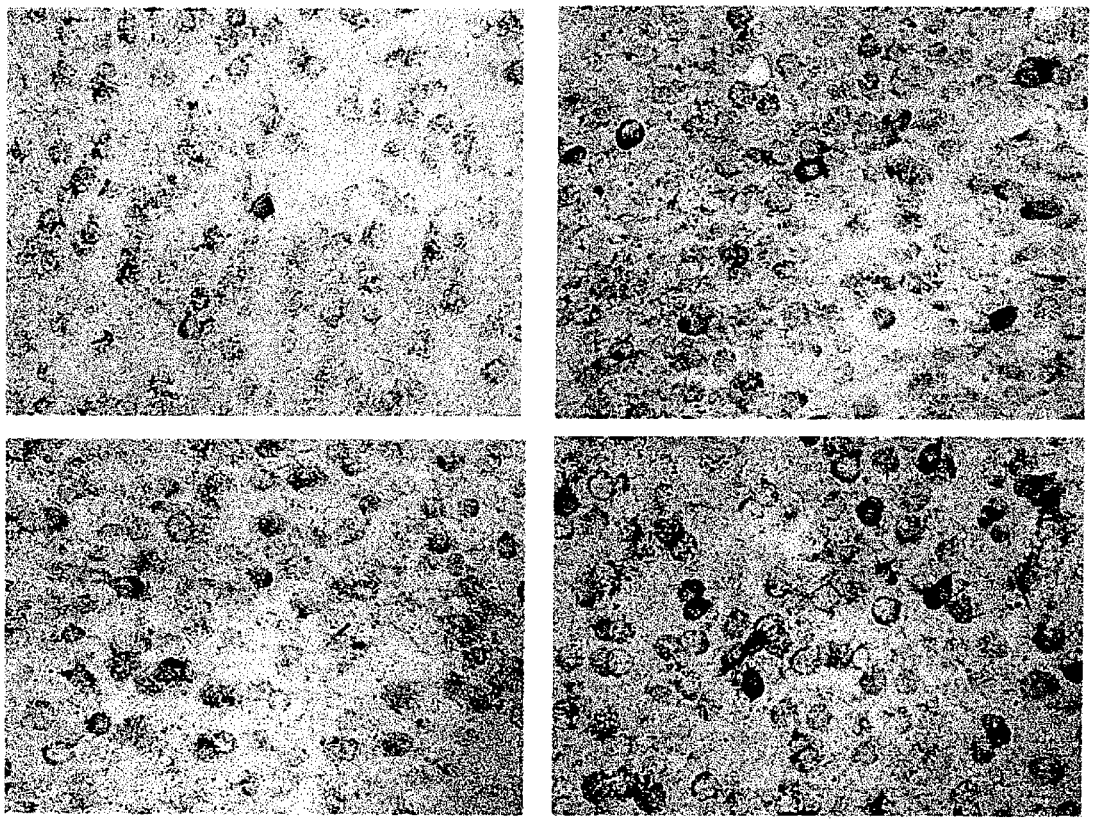
FIGS. 13A and 13B are photographs of Cat D immunoreactivity in the brains of normal mice infused with vehicle (FIG. 13A) or leupeptin (FIG. 13B).
FIGS. 13C and 13D are photographs of Cat D immunoreactivity in the brains of Ts65Dn mice infused with vehicle (FIG. 13C) or leupeptin (FIG. 13D).

Ts65Dn and control mice were infused intraventricularly with leupeptin (5 mg/ml) for 4 weeks. As previously shown in FIGS. 11C and 11D, leupeptin infusion resulted in an increased level of Cat D detected by immunolabeling in a 2N control mouse (FIG. 13B) when compared to a 2N control mouse infused with vehicle alone (FIG. 13A). The degree of lysosomal system activation, however, was found to be greater in a Ts65Dn mouse infused with leupeptin (FIG. 13D) compared with a Ts65Dn mouse infused with vehicle alone (FIG. 13C). This enhanced lysosomal system activation seen in the Ts65Dn mouse more closely mimics the lysosomal system activation seen in human AD, and is likely to make this a valuable model in which to examine the relationship between EP abnormalities, lysosomal system dysfunction, and cell death.

As a second example of the usefulness of inducing lysosomal system dysfunction by protease inhibitor infusion, we treated $PS1_{M146L}$/APPswe transgenic mice, an established model of AD-like pathology (Duff et al., Nature 383:710–713, 1996). Infusion pumps containing 5 mg/mL leupeptin were implanted into $PS1_{M146L}$/APPswe transgenic mice at 1 year of age. Animals were sacrificed 4 weeks later.

Figure 14:
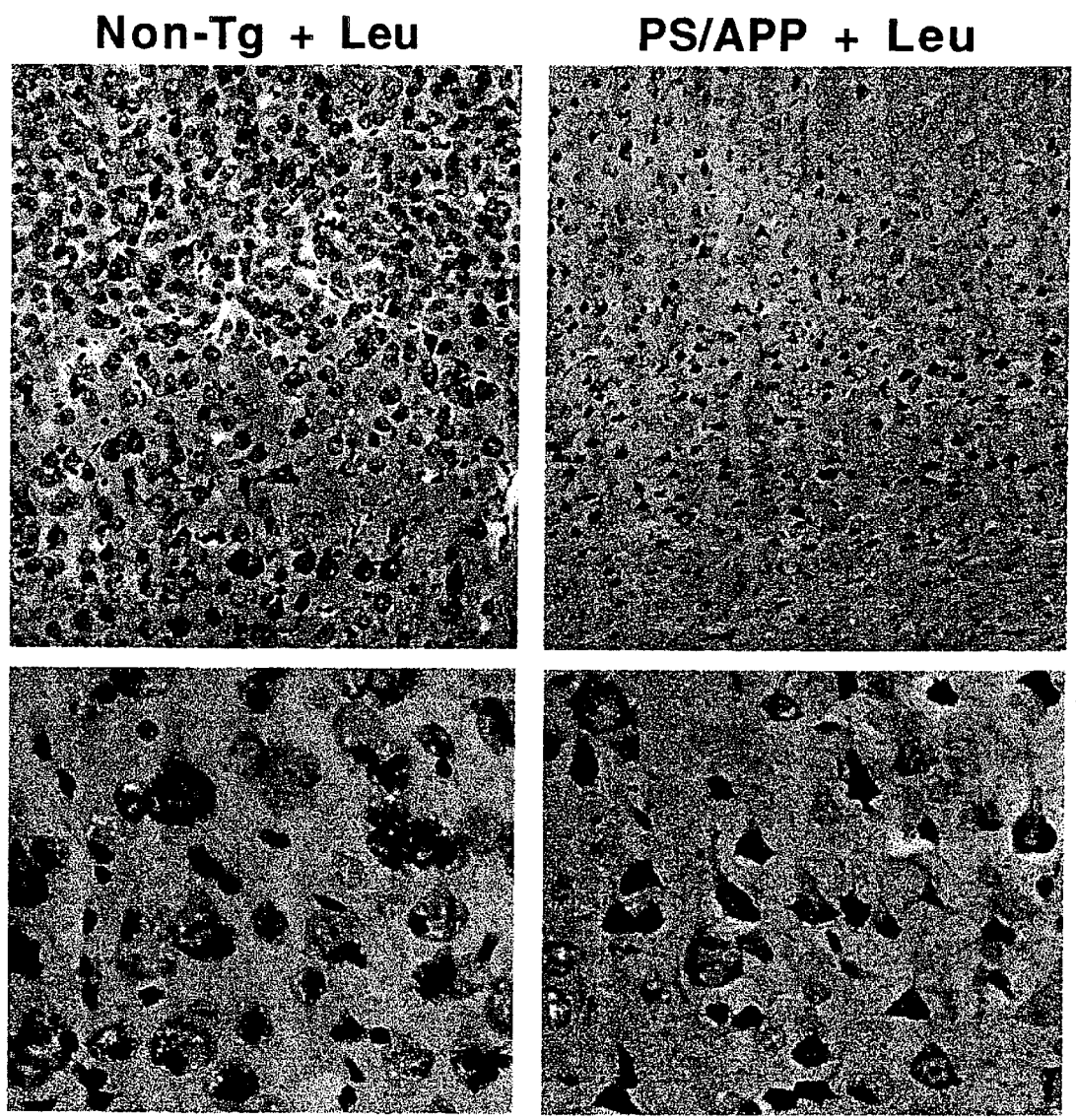
FIGS. 14A-14D are photographs of Nissl staining of brain sections of a non-transgenic mouse infused for 4 weeks with leupeptin (FIGS. 14A and 14C) and of a $PS_{M146L}/APP_{swe}$ transgenic mouse infused for 4 weeks with leupeptin (FIGS. 14B and 14D).
Figure 15:
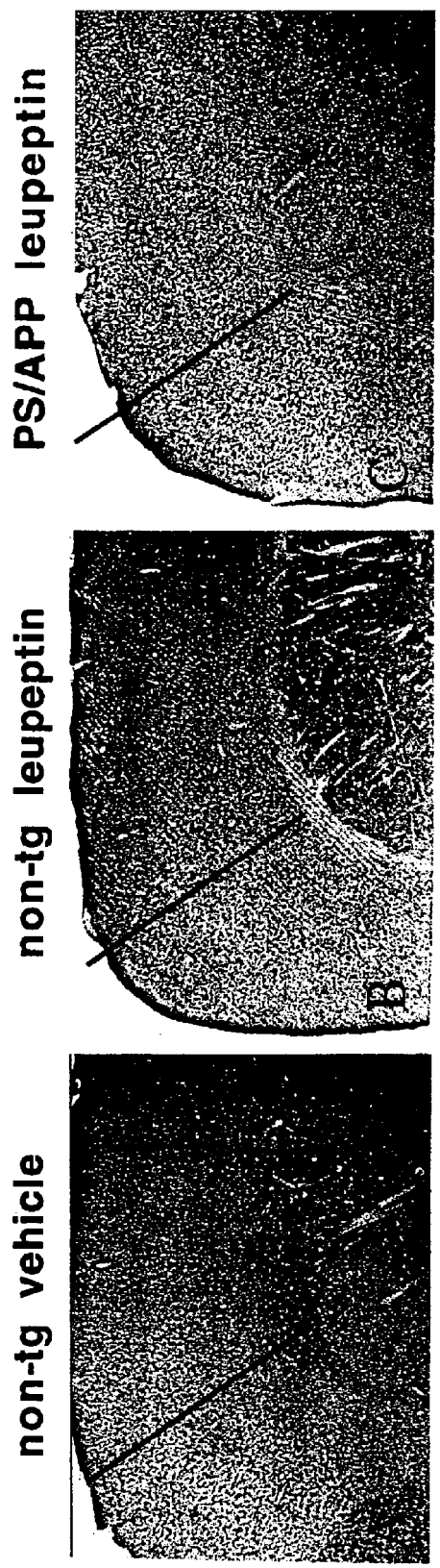
FIGS. 15A-15C are photomicrographs at low modification showing Nissl staining the extent of the cortical mantle in a non-transgenic mouse infused with vehicle (FIG. 15A), a non-transgenic mouse infused with leupeptin (FIG. 15B), and a $PS_{M146L}$/APPswe transgenic mouse infused with leupeptin (FIG. 15C).

Nissl staining of a $PS_{M146L}$/APPswe mouse infused with leupeptin showed substantial cortical neuronal hypotrophy, chromatolysis and possibly loss of neurons (FIGS. 14B and 14D), when compared to a non-transgenic littermate also infused with leupeptin (FIGS. 14A and 14C). We confirmed this observation by measuring the thickness of the cortical mantle in these mice (FIG. 15). While leupeptin treatment resulted in a small decrease in thickness of the cortical mantle of a non-transgenic mouse (compare FIGS. 15A and 15B), leupeptin treatment of a $PS1_{M146L}$/APPswe mouse reduced the thickness of the cortex by over 20%. One current limitation of the existing mouse models of AD is their failure to show substantial neuronal atrophy and/or neuronal cell loss, key features of the disease in humans. Our results strongly suggest that disruption of the lysosomal system will enhance existing animal models of AD pathology by generating a neuronal phenotype much closer to that of the human tissue.

Leupeptin Infusion Increases Amyloid Deposition and Aβ Levels

Infusion pumps and brain cannulae containing 5 mg/mL leupeptin were implanted into mice. Following four weeks of leupeptin treatment, mice were sacrificed and fixed tissue examined for lipofuscin autofluorescence, an indication of reduced lysosomal hydrolysis and accumulation of nondegraded material. There was an increase in lipofuscin autofluorescence in leupeptin-treated mice (FIG. 9B) when compared to animals receiving vehicle (20 mM HEPES) alone (FIG. 9A). Additionally, Cat D, a protease not directly affected by leupeptin, was examined in these mice. Immunolabeling of tissue sections with antibodies specific for Cat D showed a substantial increase in Cat D expression within neurons of leupeptin-treated animals (FIGS. 9C and 9D). Western blot analysis of the contralateral hemisphere to cannula placement confirmed this finding. Expression of both the mature form and heavy chain of Cat D was found to be increased (FIG. 9E). Finally, Cat D activity was measured in these same brains and found to be increased 3-fold in the leupeptin-treated mice over mice that received vehicle alone (FIG. 9F). Similar increases in Cat B immunolabeling and expression by Western blot analysis have been seen in leupeptin-treated mice, as has an increase in lysosomal acid phosphatase activity.

We also performed protease inhibitor infusion experiments in $PS1_{M146L}$/APPswe transgenic mice. Infusion pumps containing either 2 mg/mL pepstatin or 10 mg/mL leupeptin were implanted into $PS1_{M146L}$/APPswe transgenic mice at 8 weeks of age. Animals were sacrificed at 12 weeks of age, and total Aβ levels were determined by ELISA following formic acid extraction (FIG. 10A). Total Aβ levels in the pepstatin-treated mice were found to be reduced to half the level detected in untreated 12 week old PS1$_{M146L}$/ APPswe transgenic mice. Leupeptin treatment, on the other hand, increased total Aβ by 1.8 times when compared to untreated mice. We have additionally measured the activity of Cat D in the brains of untreated, pepstatin-treated, or leupeptin-treated mice (FIG. 10B). As we predicted, infusion of the aspartyl-protease inhibitor pepstatin reduced activity of Cat D in the brain. Treatment with leupeptin, a cysteine protease inhibitor, increased Cat D activity, consisent with the known role of cysteine cathepsins in degrading Cat D in the lysosome.

Figure 11:
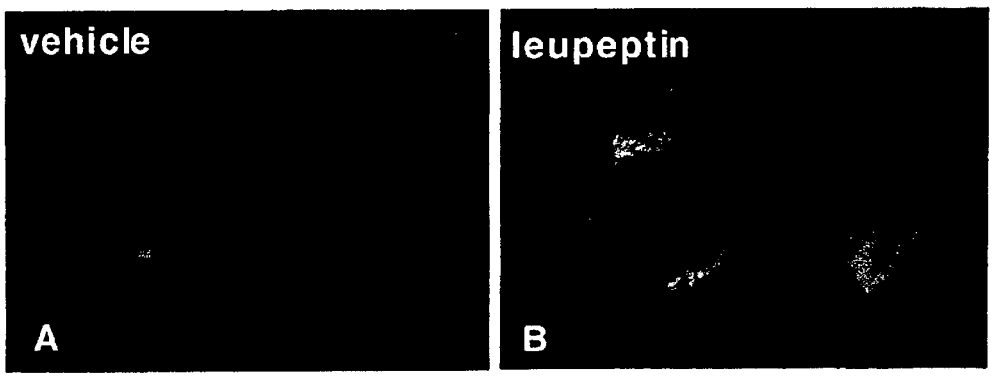
FIGS. 11A and 11B are photographs showing lipotuscin autofluorescence in sections of leupeptin-treated but not vehicle-treated brains.
FIGS. 11C and 11D are photographs showing increased Cat D immunolabeling in sections of leupeptin-treated vs. vehicle-treated brains.
FIG. 11E is a photograph of a Western blot showing increased Cat D protein levels in the brain of leupeptin-treated mice when compared to control mice.
FIG. 11F is a schematic illustration showing increased Cat D activity in the brains of leupeptin-treated mice when compared to control mice.
Figure 11:
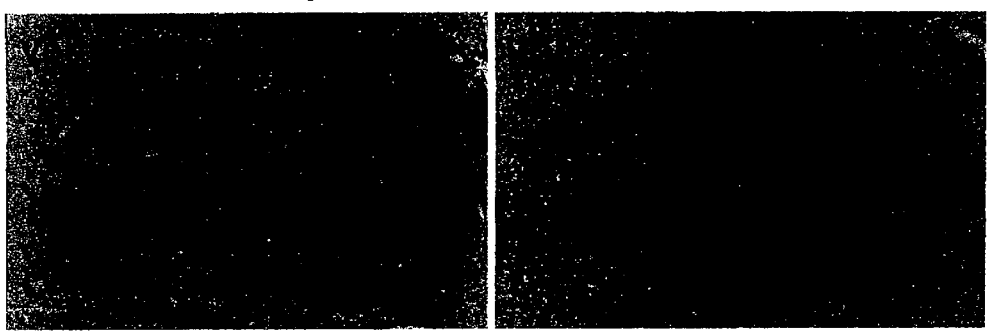
Figure 11:
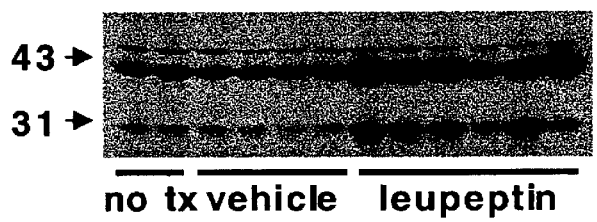
Figure 11:
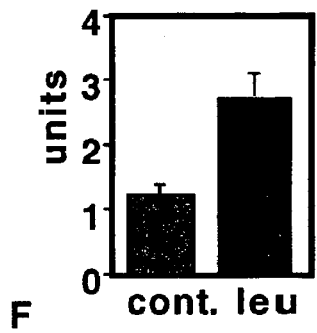

Additionally, Western blot analysis of the cytoskeletal associated protein tau in brain revealed an increase in lower molecular weight forms of the protein (Mr~30–34 kDa) in leupeptin-infused mice, suggesting an important lysosomal component to tau processing in neurons (FIG. 11).

Test Compounds and Extracts

In general, compounds are identified from large libraries of both natural product extracts and synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PhannaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-pathogenic activity should be employed whenever possible.

When a crude extract is found to decrease activity of the endocytic pathway, further fractionation of the positive lead extract is necessary to isolate chemical constituents responsible for the observed effect. Thus, the goal of the extraction, fractionation, and purification process is the careful characterization and identification of a chemical entity within the crude extract having the desired activity. Methods of fractionation and purification of such heterogenous extracts are known in the art. If desired, compounds shown to be useful agents for the treatment of pathogenicity are chemically modified according to methods known in the art.

Uses

For therapeutic uses, the compounds, compositions, or agents identified using the methods disclosed herein may be administered systemically, for example, formulated in a pharmaceutically-acceptable buffer such as physiological saline. Treatment may be accomplished directly, e.g., by treating the animal with antagonists which disrupt, suppress, attenuate, or neutralize the biological events associated with AD. Preferable routes of administration include, for example, inhalation or subcutaneous, intravenous, interperitoneally, intramuscular, intraventricular infusion, or intradermal injections which provide continuous, sustained levels of the drug in the patient. Treatment of human patients or other animals will be carried out using a therapeutically effective amount of a compound in a physiologically-acceptable carrier. Suitable carriers and their formulation are described, for example, in Remington's *Pharmaceutical Sciences* by E. W. Martin. The amount of the compound to be administered varies depending upon the manner of administration, the age and body weight of the patient, and with the type of disease and extensiveness of the disease. A compound is administered at a dosage that decreases activity of the endocytic pathway. For example, for systemic administration a compound is administered typically in the range of 0.1 ng–10 g/kg body weight.

Assays

Using transfected cells and in vivo models described herein, candidate compounds can be assayed for their ability to reduce the alterations in endocytosis and hydrolase trafficking to early endosomes observed in human brain. Additionally, candidate compounds can be assayed for their ability to decrease Aβ production. These assays are described in more detail below.

Measurements of Endocytosis

Early endosomal volumes and identities of modulator proteins associated with increased endocytosis are determined by immunolabeling (e.g., by Western blot analysis) with rab5, rabaptin 5, or EEA 1, using standard techniques.

Fluid-phase endocytosis rates are determined by incubating living cells in 5 mg/ml of dextran in DMEM for various time periods (5 min to 2 hr). Rates of uptake are determined visually using fluorescent-dextran or, alternatively, quantitatively using biotin-dextran coupled to a colorometric assay (Prchla et al., J. Cell Biol. 131:111–123, 1995).

Receptor mediated uptake is assayed by binding fluorescent-labeled transferrin (Cy3-transferrin, 25 μg/ml) at 4° C. for 1 hr to living cells followed by warming to 37° C. for periods of 0, 3, 6, 8, and 20 min. Cells fixed after 6 min, which we have found to have maximum uptake into early endosomes, are quantitated for the number of Cy3-positive endosomes. In addition, double labeling experiments are performed to show the coincidence of Cy3-transferrin and rab5. In these assays, it is preferred that transformed cells are compared to parental cells.

Localization of Lysosomal Hydrolases to Early Endosomes

Double-labeling with the specific antibodies (rab5 and Cat D or Cat B) and confocal microscopy are used to show coincidence of lysosomal hydrolases and early endosomes. Uptake of BODIPY-pepstatin, which specifically binds to enzymatically active Cat D, is a useful method to detect increased Cat D levels in early endosomes. 1 mM BODIPY-pepstatin is added to the growth medium, and cells washed at various time-points (10 min to 5 hr), fixed, and labeled with antibodies specific for early endosomes and examined as above. The specificity of increased BODIPY-pepstatin uptake is determined by including an excess of unlabeled pepstatin in the medium (20 mM). Cat D and Cat B are immunoprecipitated from cell lysates and from the growth medium using specific antibodies. In parallel cultures, 5 mM Man-6-P is added to the chase medium, to promote secretion of hydrolases delivered to the cell surface/early endosomes into the medium (Watanabe et al., Proc. Natl. Acad. Sci. USA 87:8036–8040, 1990).

A mouse from a transgenic line that is administered a candidate compound is analyzed to determine whether it exhibits evidence of decreased endocytosis or less mistrafficking of hydrolases to early endosomes compared to a transgenic mouse from the same line but not given a candidate compound. This can be performed using any of the assays described herein. In one example, sections of mouse brain are assessed by labeling with antibodies to rab5, Cat D, and MPR46. Whether endocytosis is decreased in the transgenic mice administered the compound can be determined using semiquantitative densitometry. The transgenic mice described herein can be crossed with each other, with a mouse that has increased AD-like pathology, a mouse that is expressing a polypeptide that has a mutation found in human with AD (e.g., APP, PS-1, or PS-2), or with a reporter mouse. Transgenic mice from these crosses that have been administered a candidate compound are examined, for example, at 2, 5.5, or 12 months of age.

Aβ ELISA Methods

The Aβ sandwich ELISA is generally known to those skilled in the art, with both Aβ ELISA kits (Biosource International, Camavillo, Calif.) and appropriate antibodies (e.g., 4G8, GE10; Seneteck, PLC, Napa, Calif.) available commercially. For the Aβ sandwich ELISA, Nunc-Immuno Plates (Nunc A/S Roskilde, Denmark) were coated overnight at 4% using antibodies specific for Aβ40 or Aβ42 in 100 mM bicarbonate buffer, pH 9.6. Remaining protein binding sites were blocked by incubating with 1% Block Ace (Yukijirushi Milk, Sapporo Japan) in PBS for 4 hours at room temperature. 10% (w/v) homogenates were prepared from a hemibrain in 20 mM Tris, 250 mM sucrose, 1 mM EDTA, 1 mM EGTA, protease inhibitors, pH 7.4, and stored frozen at −70° C. Immediately prior to being loaded on the ELISA, 1 ml of the brain homogenate was extracted in diethylamine (Sigma, St. Louis, Mich.) by adding an equal volume of 0.4% DEA in 100 mM NaCl, re-homogenized, and centrifuged for 1 hour at 100,000× g. The supernatant was collected, neutralized with 0.1 volume 0.5 M Tris, pH 6.8, and loaded in duplicate wells both neat and diluted 1:2 in EC buffer (20 mM Na phosphate, 2 mM EDTA, 400 mM NaCl, 0.2 BSA, 0.4% Block Ace, 0.95% CHAPS). The DEA extraction protocol has been shown to efficiently recover immunoreactive Aβ from mouse brain homogenates and leave both full-length and sAPP in the 100,000× g pellet (Savage et al., J. Neurosci. 18:1743–1752, 1998). Alternatively, conditioned media collected from cells was loaded neat and 1:2. Aβ-40 and Aβ-42 peptide standards were purchased from American Peptide Co. (Sunnyvale, Calif.), stored at −70° C., and diluted in EC buffer immediately prior to use. ELISA plates were incubated overnight at 4° C. with samples and standards. Aβ was detected by incubating for 4 hours at room temperature with an HPR-conjugated anti-Aβ antibody in 20 mM Na phosphate, 2 mM EDTA, 400 mM NaCl, 1.0% BSA. ELISA plates were developed using a color reaction (ABTS Peroxidase Substrate System, Kirkegaard & Perry, Gaithersburg, Md.) and the $OD_{450}$ read.

Isolation of Early Endosomes

Early endosomes are isolated from brain using standard techniques (e.g., the Optiprep step gradient density method (Ford et al., Anal. Biochem. 220:360–366, 1994; Graham et al., Anal. Biochem. 220:367–373, 1994; Kindberg et al., Anal. Biochem. 142:455–462, 1984)).

Cell Lines

L-cells and N2a cells are maintained at 37° C. and 5% $CO_2$ in high glucose DMEM supplemented with 10% FBS, 2 mM glutamax I, and penicillin/streptomycin. For selection, medium is supplemented with 400 μg/ml of G418, 200 μg/ml of hygromycin B, and/or HAT as is appropriate. IMR-32 neuroblastoma cells are maintained in 60% DMEM, 30% Ham's-F12, 5% α MEM, 1% FCS, 4% NCS, 0.6% glucose, 200 mM glutamine, and 15 mM HEPES. Neuronal differentiation is achieved by supplementing medium with 1 mM dibutyryl cAMP and 2.5 μM 5-BDU.

Immunofluorescence Labeling

Transfected cells are incubated in 20 mM butyrate in growth medium for 24–48 hr prior to fixation to induce expression of transfected cDNA and fixed in 4% PFA, 5% sucrose in PBS (pH 7.3) at RT for 20–35 min, rinsed, and labeled with specific antibody in PBS containing 10% serum with 0.1% saponin. Coverslips are washed after primary antibody binding and secondary antibody is bound for 2 hr at RT. The coverslips are then be rinsed, mounted and examined by immunofluorescence.

Metabolic Labeling

Approximately $5 \times 10^5$ cells are seeded in 35 mm dishes for 16 hr, followed by neuronal differentiation and/or induction of expression of transfected cDNA. Cells are incubated in methionine- and cysteine-free DMEM for 20 min before a 15-minute incubation with 100–200 μCi/mL TRANS$^{35}$S-LABEL (Dupont-NEN), or for 4 hr with 500 μCi/ml for Aβ IP. Following rinses with DMEM 10% FBS and 2 mM methionine at 4° C., cells are lysed immediately or incubated with 2 mM unlabeled methionine in DMEM with 10% FBS for chase periods of 15 min to 8 hr. APP and APP metabolites are immunoprecipitated using any of a number of antibodies known to those skilled in the art, followed by separation using SDS-PAGE. Gels are exposed to X-ray film or are analyzed quantitatively using a Phosphoimager.

Immunocytochemistry and Digital Confocal Microscopic Analysis

Sections of fixed transgenic mouse brain or fixed cultured cells are processed as previously described (Cataldo et al., Neuron 14: 671–680, 1995; Cataldo et al., J. Neuropathol. Exp. Neurol. 55: 704–715, 1996; Cataldo et al., Adv. Exp. Med. Biol. 389: 271–280, 1996; Cataldo et al., J. Neurosci. 16: 186–199, 1996; Cataldo et al., Proc. Natl. Acad. Sci. USA 87: 3861–3865, 1990; Cataldo et al., Brain Res. 513: 181–192, 1990; Nixon et al., Ann. N.Y. Acad. Sci. 674: 65–88, 1992). Ts65Dn mice made transgenic for human APOE ε2 and ε4, as well as other transgenic mouse models described herein, are studied initially by immunocytochemical analysis with rab5, rabaptin 5 and EEA 1 to determine if the APOE genotype accentuates morphological changes in early endosomes. The effect of ApoE on exacerbating EP changes is further examined by crossing APOE allele-specific mice with Ts65Dn mice.

Additional Methods

A compound that decreases the activity of the EP can be further tested for AD-like abnormalities in physiology, anatomy, or behavior using assays known to those skilled in the art, including those described in U.S. Pat. No. 5,877,399, hereby incorporated by reference.

Other Embodiments

All publications mentioned in this specification are herein incorporated by reference to the same extent as if each independent publication was specifically and individually indicated to be incorporated by reference.

While the invention has been described in connection with specific embodiments thereof, it will be understood that it is capable of further modifications. This application is intended to cover any variations, uses, or adaptations following, in general, the principles of the invention and including such departures from the present disclosure within known or customary practice within the art to which the invention pertains and may be applied to the essential features hereinbefore set forth.

What is claimed is:

1. A method for identifying a candidate compound as a compound that may be useful for the treatment of Alzheimer's disease, said method comprising the steps of:
   (a) providing a cell in vitro expressing a recombinant rab5 nucleic acid that increases activity of the endocytic pathway;
   (b) contacting said cell with a candidate compound; and
   (c) measuring said activity, wherein a decrease in said activity, relative to the activity of the endocytic pathway in a cell expressing the recombinant nucleic acid but not contacted with the candidate compound, identifies the candidate compound as a compound that may be useful for the treatment of Alzheimer's disease.

2. The method of claim 1, wherein said activity of the endocytic pathway is selected from the group consisting of endosomal fusion, endosomal recycling, expression of MPR46, accumulation of lysosomal hydrolases in early endosomes, and accumulation of Aβ in early endosomes.

3. The method of claim 1, wherein said cell is from a cell line selected from the group consisting of a fibroblast cell line, a neuronal cell line, and a neuroblastoma cell line.

4. The method of claim 1, wherein said cell is selected from the group consisting of a fibroblast, a neuron, and an endothelial cell.

5. A method for identifying a candidate compound as a compound that may be useful for the treatment of Alzheimer's disease, said method comprising the steps of:
   (a) providing a cell in vitro expressing a recombinant rab5 nucleic acid that increases activity of the endocytic pathway;
   (b) contacting said cell with a candidate compound; and
   (c) measuring Aβ formation, wherein a decrease in Aβ formation, relative to Aβ formation by a cell expressing the recombinant nucleic acid but not contacted with the candidate compound, identifies the candidate compound as a compound that may be useful for the treatment of Alzheimer's disease.

6. The method of claim 5, wherein said cell is from a cell line selected from the group consisting of a fibroblast cell line, a neuronal cell line, and a neuroblastoma cell line.

7. The method of claim 5, wherein said cell is selected from the group consisting of a fibroblast, a neuron, and an endothelial cell.

* * * * *

UNITED STATES PATENT AND TRADEMARK OFFICE
CERTIFICATE OF CORRECTION

PATENT NO. : 6,838,592 B1  
APPLICATION NO. : 09/560124  
DATED : January 4, 2005  
INVENTOR(S) : Nixon et al.

Page 1 of 1

It is certified that error appears in the above-identified patent and that said Letters Patent is hereby corrected as shown below:

Column 1, Line 37, replace "targetted" with --targeted--.

Column 4, Line 63ff., replace "immunof-luorescence" with --immuno-fluorescence--.

Column 6, Line 13, replace "APPswe" with --$APP_{swe}$--.

Column 7, Line 66, replace "hemagglutinin" with --hemaglutinin--.

Column 9,  
Line 28, replace "mouse Any" with --mouse. Any--;  
Line 33ff., replace "endot-helial" with --endo-thelial--; and  
Line 51, replace "homogozygous" with --homozygous--.

Column 10,  
Line 20, replace "coverstips" with --coverslips--; and  
Line 64, replace "homoguates" with --homogenates--.

Column 12, Line 15ff., replace "pro-ductiondeposition" with -- pro-duction deposition--.

Column 18, Line 26, replace "then be rinsed" with --then rinsed--.

Signed and Sealed this

Fifteenth Day of August, 2006

JON W. DUDAS  
*Director of the United States Patent and Trademark Office*